(12) United States Patent
Damren et al.

(10) Patent No.: US 9,340,763 B2
(45) Date of Patent: May 17, 2016

(54) TEMPERATURE CONTROLLING SURFACES AND SUPPORT STRUCTURES

(71) Applicant: GE HEALTHCARE BIO-SCIENCES CORP., Piscataway, NJ (US)

(72) Inventors: Richard L. Damren, Marlborough, MA (US); Thomas Erdenberger, Arlington, MA (US); Colin R. Tuohey, Medway, MA (US); Joseph D. Crowell, South Hamilton, MA (US); Parrish M. Galliher, Littleton, MA (US); Kenneth P. Clapp, Marlborough, MA (US); Peter A. Mitchell, East Greenwich, RI (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 241 days.

(21) Appl. No.: 13/691,998

(22) Filed: Dec. 3, 2012

(65) Prior Publication Data
US 2013/0089925 A1  Apr. 11, 2013

Related U.S. Application Data

(63) Continuation of application No. 12/410,724, filed on Mar. 25, 2009, now abandoned.

(60) Provisional application No. 61/039,382, filed on Mar. 25, 2008, provisional application No. 61/566,187, filed on Dec. 2, 2011, provisional application No. 61/586,398, filed on Jan. 13, 2012.

(51) Int. Cl.
*B01J 8/00* (2006.01)
*C12M 1/00* (2006.01)
(Continued)

(52) U.S. Cl.
CPC ............ *C12M 23/26* (2013.01); *B01F 15/0085* (2013.01); *B01J 19/006* (2013.01); *B01J 19/18* (2013.01); *B01J 19/24* (2013.01);
(Continued)

(58) Field of Classification Search
CPC ............................ B01J 2219/24; C12M 23/28
See application file for complete search history.

(56) References Cited

U.S. PATENT DOCUMENTS 3,963,690 A * 6/1976 Pruitt et al. .................... 526/65
4,282,861 A * 8/1981 Roark ................. F24D 17/0021
                                                              122/32
(Continued)

FOREIGN PATENT DOCUMENTS

WO       WO 01/78890        10/2001
WO       WO 2008/088371      7/2008

OTHER PUBLICATIONS

Search Report Dated May 8, 2014 Issued on Corresponding International Application No. PCT/US2013/072742 by the European Patent Office.

*Primary Examiner* — Jyoti Nagpaul
(74) *Attorney, Agent, or Firm* — Grogan, Tuccillo & Vanderleeden, LLP

(57) ABSTRACT

A heat exchange module for use in a chemical, pharmaceutical or biological reactor system can include a body configured to be disposed in the reactor system having an inner replaceable reactant container is disclosed. The body can further include at least one thermally conductive surface adapted to contact the inner replaceable reactant container to facilitate heat transfer. Furthermore, the heat exchange module can include a heat exchanger disposed within the module body and can include a fluid circulation path through which a heat exchange fluid can be circulated.

18 Claims, 19 Drawing Sheets

(51) Int. Cl.
    C12M 1/02    (2006.01)
    B01F 15/00   (2006.01)
    B01J 19/00   (2006.01)
    B01J 19/18   (2006.01)
    F28F 3/12    (2006.01)
    F28F 13/06   (2006.01)
    F28D 1/06    (2006.01)
    F28D 1/02    (2006.01)
    B01J 19/24   (2006.01)
    B65D 30/08   (2006.01)
    F16L 11/04   (2006.01)
    F28D 1/047   (2006.01)
    F28F 9/013   (2006.01)
    F28D 7/02    (2006.01)
    F28D 21/00   (2006.01)
    F28F 13/00   (2006.01)

(52) U.S. Cl.
    CPC .............. *B65D 31/02* (2013.01); *C12M 23/14* (2013.01); *C12M 23/28* (2013.01); *C12M 27/20* (2013.01); *C12M 41/18* (2013.01); *C12M 41/24* (2013.01); *F16L 11/04* (2013.01); *F28D 1/0213* (2013.01); *F28D 1/047* (2013.01); *F28D 1/06* (2013.01); *F28D 7/024* (2013.01); *F28D 7/026* (2013.01); *F28F 3/12* (2013.01); *F28F 9/0131* (2013.01); *F28F 13/06* (2013.01); *B01J 2219/0002* (2013.01); *B01J 2219/0009* (2013.01); *B01J 2219/00081* (2013.01); *B01J 2219/00085* (2013.01); *B01J 2219/00094* (2013.01); *B01J 2219/00765* (2013.01); *B01J 2219/00768* (2013.01); *B01J 2219/24* (2013.01); *F28D 2021/0077* (2013.01); *F28D 2021/0078* (2013.01); *F28F 2013/006* (2013.01); *F28F 2255/02* (2013.01)

(56) References Cited

U.S. PATENT DOCUMENTS

2008/0068920 A1* 3/2008 Galliher .............. B01F 3/04106
                                                           366/102
2009/0242173 A1  10/2009 Mitchell et al.

* cited by examiner

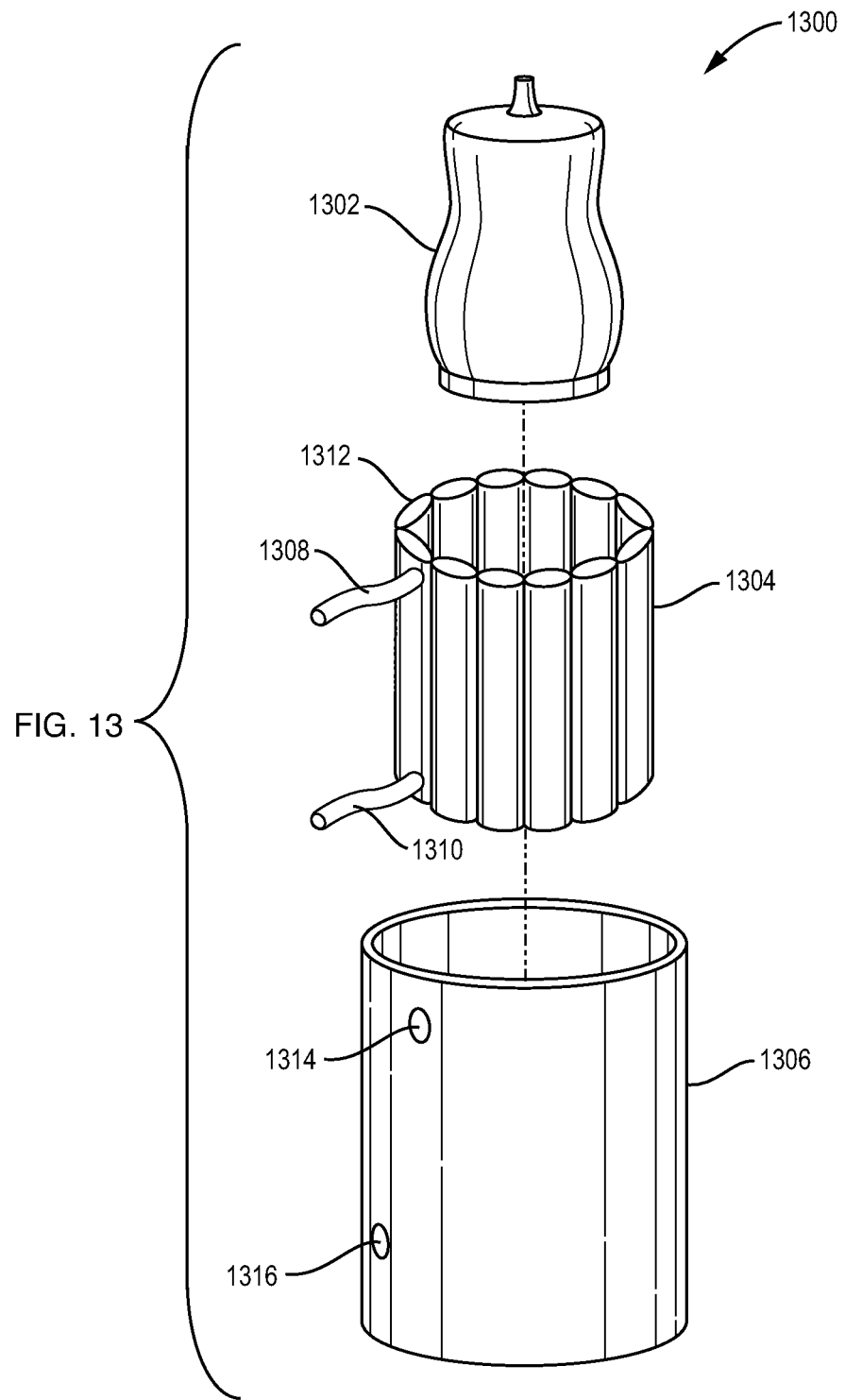

TEMPERATURE CONTROLLING SURFACES AND SUPPORT STRUCTURES

RELATED APPLICATIONS

This application claims the priority benefit of U.S. Provisional Application Nos. 61/566,187 filed on Dec. 2, 2011, and 61/586,398 filed on Jan. 13, 2012, the teachings of each are incorporated herein by reference in their entirety. This application is also a continuation-in-part of U.S. patent application Ser. No. 12/410,724 filed Mar. 25, 2009, which claims the priority benefit of U.S. Provisional Application No. 61/039,382 filed on Mar. 25, 2008, the teachings of each are also incorporated herein by reference in their entirety.

FIELD OF INVENTION

This disclosure relates generally to biochemical processing systems and methods and, in particular, to systems for controlling temperature of a reactor vessel.

BACKGROUND

A variety of vessels for manipulating fluids and/or for carrying out chemical or biological reactions are available. For example, biological materials such as mammalian, plant or insect cells and microbial cultures can be processed using traditional or disposable bioreactors. Although such bioreactors and other fluid manipulating systems incorporating temperature control systems are known, there is a need for improvements to such systems.

Because microbial cultures grow and multiply twenty to forty (20 to 40) times faster than mammalian cells, both the oxygen consumption and the heat evolution rates of a microbial cultures are about 20 to 40 times greater than that of mammalian fermentation processes. In order to sustain growth in microbial cultures, the bioreactor for microbial systems must therefore be able to supply oxygen to the culture fluid and remove heat from the culture fluid 20 to 40 times faster than the oxygen supply and heat removal rates for mammalian cell cultures. This is accomplished in stainless steel microbial fermentors through a number of means, including, e.g., very vigorous agitation by multiple impellers to disperse air bubbles and increase absorption of oxygen by the cells; very high flow rates of air to supply more oxygen; extra cooling surfaces such as cooling coils to remove from the culture fluid the large amount of heat that is generated by the metabolism of the microbial cells and by the frictional heat generated by the vigorous agitation. However, in single-use bioprocessing bags, heat removal is an ongoing problem, especially for microbial bioreactors.

As is well known by those of skill in the field of polymeric or plastic materials such as films and flexible bags, polymeric or plastic films are relatively very poor conductors of heat. Therefore, cooling a fluid inside a vessel containing a replaceable container, e.g., a flexible plastic bag, may require specific modification of the cooling surfaces of the flexible bag and/or the vessel. There is an ongoing need for systems and methods to improve the removal of the large amount of heat generated by microbial cell cultures.

SUMMARY OF THE INVENTION

Methods and apparatus are disclosed for use in a chemical, pharmaceutical or biological reactor system for temperature control. In one aspect, the invention includes a heat exchange module that can be disposed in a reactor system having an inner replaceable reactant container such as, for example, a flexible bag or a semi-rigid container.

One embodiment of the invention is a heat exchange module for use in a chemical, pharmaceutical or biological reactor system, comprising: a body configured to be disposed in a reactor vessel comprising a support structure, the reactor vessel having an inner replaceable or single use reactant container, the body comprising at least one surface configured to conform to a shape of the reactor vessel and at least one thermally conductive surface adapted to contact the inner replaceable container to facilitate heat transfer, and a heat exchanger disposed within the module body comprising a fluid circulation path through which a heat exchange fluid can be circulated.

Another embodiment of the invention is a heat exchange module for use in a chemical, pharmaceutical or biological reactor system, comprising: a body configured to be disposed in a reactor vessel comprising a support structure and having an inner replaceable or single use reactant container, the body further comprising at least one thermally conductive surface adapted to contact the inner replaceable reactant container to facilitate heat transfer, and a heat exchanger disposed within the module body comprising a fluid circulation path through which a heat exchange fluid can be circulated.

Also disclosed herein is a flexible bioreactor or mixer bag comprising at least one double wall portion comprising serpentine fluid flow channels within the double wall portion.

Another aspect of the invention is a container chosen from a flexible bioreactor bag, a flexible mixer bag, and a flexible tubing, the container comprising at least one double wall portion comprising an inner and an outer wall and a heat conductive material attached to a portion of at least one of the inner wall and the outer wall.

Yet another aspect of the invention is a flexible polymeric wall chosen from a bioreactor wall, a mixer wall, and a tubing wall, the flexible wall comprising a heat conductive material attached to a portion of the flexible wall.

Yet another embodiment the invention is a jacketed, tiered baffle, bioreactor tank comprising: an outer cylindrical-shaped jacket; and a cylindrical tank having an inner tank surface defining a chamber configured for supporting a flexible bag disposed within the chamber, and an outer tank surface having tiered baffles configured for routing a liquid coolant around the entirety of the outer tank surface, the cylindrical tank disposed axially within the outer cylindrical-shaped jacket, wherein the outer cylindrical-shaped jacket is sealed to the cylindrical tank in a manner sufficient to prevent or minimize loss of the liquid coolant. A flexible bioprocessing bag can be placed within a jacketed, tiered baffle, bioreactor tank in order to be cooled by the circulating coolant in the jacket.

BRIEF DESCRIPTION OF THE DRAWINGS

The foregoing and other non-limiting objects, features and advantages of the invention will be apparent from the following more particular description of illustrative embodiments of the invention, as illustrated in the accompanying drawings in which like reference characters refer to the same parts throughout the different views. The drawings are schematic and not intended to be drawn to scale, emphasis instead being placed upon illustrating the principles of the invention. The drawings are schematic and not intended to be drawn to scale, emphasis instead being placed upon illustrating the principles of the invention. The features illustrated or described in connection with one exemplary embodiment can be combined with the features of other embodiments. Such modifications and variations are intended to be included within the scope of the present invention.

FIG. 13 is an exploded view of an exemplary heat exchange module including a liner.

DETAILED DESCRIPTION

Figure 1:
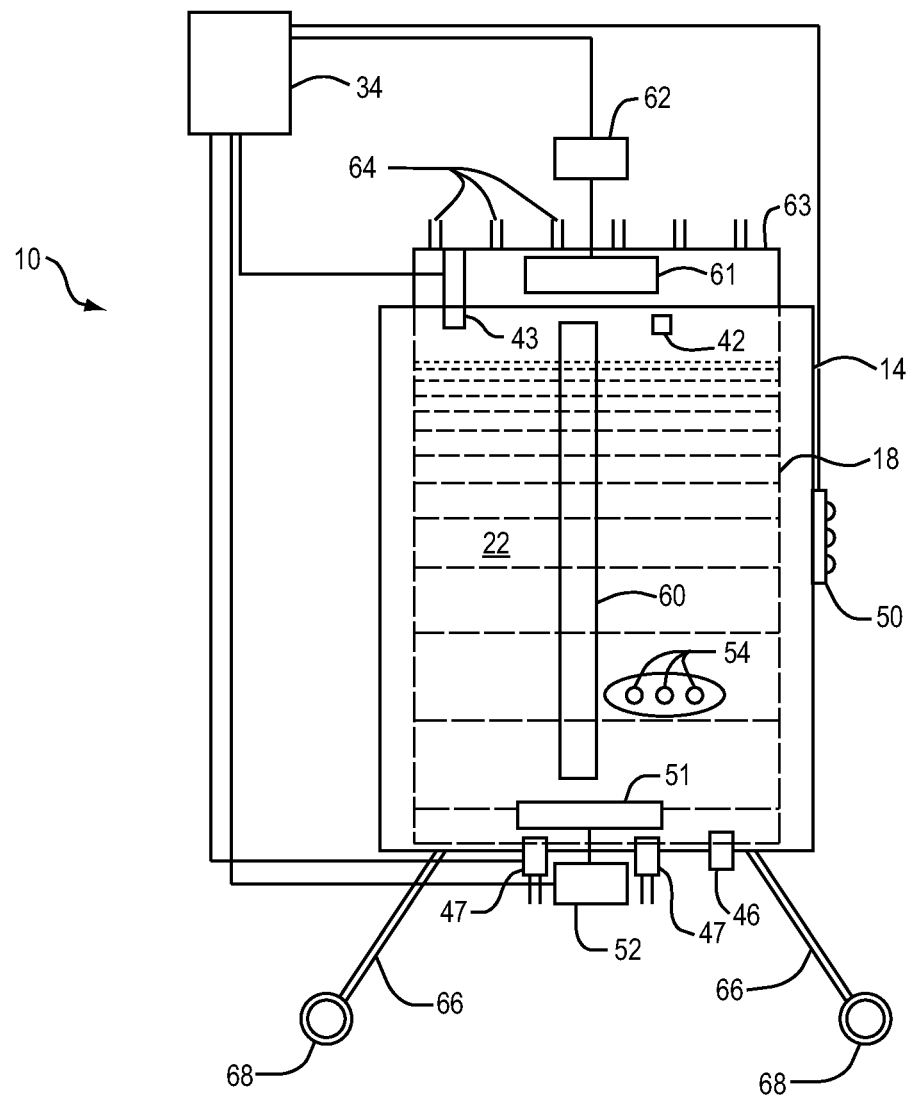
FIG. 1 is a schematic representation of a system comprising a container contained within a support structure according to one embodiment of the invention.

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "e.g.," and "in one embodiment."

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but can include other elements not expressly listed or inherent to such process, article, or apparatus. Further, unless expressly stated to the contrary, "or" refers to an inclusive or and not to an exclusive "or."

Disclosed herein are systems and methods for containing and manipulating fluids, and for regulating the temperature of fluids associated with a chemical, biological, or pharmaceutical reaction or process. Certain embodiments of the invention involve a series of improvements and features for fluid containment systems, for example, by providing a vessel including a heat exchanger which can be in the form of a flexible, collapsible bag or a rigid, or semi-rigid, heat exchange module. Some embodiments of the invention include hollow baffles (interior or exterior to the liner, or both) through which coolant is circulated. Other embodiments of the invention include a jacketed, tiered baffle, bioreactor tank that provides coolant to 100% of the tank surface, conducting heat away from a flexible bag bioreactor disposed within the tank.

Although much of the description herein involves exemplary applications of the present invention related to bioreactors and chemical, reaction systems, the invention and its uses are not so limited, and it should be understood that aspects of the invention can also be used in other settings, including those involving containment systems in general, as well as systems for containment or for mixing or other processing.

The terms "rigid" and "semi-rigid" are used herein interchangeably to describe structures that are "non-collapsible," that is to say structures that do not fold, collapse, or otherwise deform under normal forces to substantially reduce their elongate dimension. Depending on the content "semi-rigid" can also denote a structure that is more flexible than a "rigid" element, e.g., a bendable tube or conduit, but still one that does not collapse longitudinally under normal conditions and forces. "Flexible container", "flexible bag", or "collapsible bag" as used herein, indicates that the container or bag is unable to maintain its shape and/or structural integrity when subjected to the internal pressures, for example, pressures resulting from the weight or hydrostatic pressure of liquids or gases contained therein without the benefit of a separate support structure. A reusable support structure such as a rigid vessel or tank can be utilized to surround and support the collapsible bag.

The term "vessel" as used herein generally refers to a support structure or tank surrounding and supporting a flexible bag. The term vessel is intended to encompass bioreactor vessels as well as other containers or conduits commonly used in biological or biochemical processing, including, for example, cell culture/purification systems, mixing systems, media/buffer preparation systems, and filtration/purification systems, e.g., chromatography and tangential flow filter systems, and their associated flow paths. In the bioprocessing industry, the term "vessel" is often used to define any enclosed bioprocessing volume in which the regulation of temperature is desirable. The terms "reactor" and "reactor system" are used interchangeably herein and are intended to encompass chemical, pharmaceutical and biological reactors, including but not limited to cell culturing and vaccine producing reactors, as known in the art.

As will be detailed below, a heat exchange module for use in a chemical, pharmaceutical or biological reactor system can include a body configured to be disposed in the reactor system between an outer support structure and an inner replaceable reactant container. The body can further include at least one thermally conductive surface adapted to contact the inner replaceable reactant container to facilitate heat transfer. Furthermore, the heat exchange module can include a heat exchanger disposed within the module body and can include a fluid circulation path through which a heat exchange fluid can be circulated. A heat exchange module can be removable from the reactor system or can be integrally formed with the reactor support structure. A heat exchange module can also be formed so as to provide increased mixing to a fluid in the interior replaceable container or to fluid circulating in the vessel. Increased mixing can increase the efficiency of heat transfer in the reactor system.

A support structure that can be used to support a collapsible bag can have any suitable shape able to surround and/or contain the bag. In some cases, the support structure is reusable. The support structure can be formed of a substantially rigid material. Non-limiting examples of materials that can be used to form the support structure include stainless steel, aluminum, glass, resin-impregnated fiberglass or carbon fiber, polymers such as high-density polyethylene, polyacrylate, polycarbonate, polystyrene, nylon or other polyamides, polyesters, phenolic polymers, and combinations thereof. The materials can be certified for use in the environment in which it is used. For example, non-shedding materials can be used in environments where minimal particulate generation is required. In addition, the support structure can include other components, such as channels, for flowing a fluid and/or containing a material to modify the properties of the support structure.

A reusable support structure or vessel can have any suitable volume and, in some instances, has a volume substantially similar to that of the container contained in the support structure. The reusable support structure can have a volume between, for example, of from about 5 liters to about 5,000 liters. Volumes greater than 10,000 liters are also possible.

In other embodiments, however, a reactor system does not include a separate container, for example, a collapsible bag and support structure, but instead comprises a self-supporting disposable container. For example, a container that can be used to hold and/or store fluids can be in the form of a plastic vessel and can optionally include an agitation system integrally or releasably attached thereto. The agitation system can be disposable along with the container. In one particular embodiment, such a system includes a magnetic impeller positioned in a polymeric container or a flexible bag and held in place by an external magnetic drive system. In another embodiment, a container that is used as a heat exchanger is in the form of a rigid container. It should therefore be understood that many of the aspects and features of the vessels described herein with reference to a container and a support structure are also applicable to a self-supporting disposable container.

As described herein a vessel such as a collapsible bag can include a mixing system for mixing contents of the vessel. In some cases, more than one agitator or impeller can be used to increase mixing power, and the impellers can be the same or different. In some cases, the agitator can be one in which the height can be adjusted, for example, such that the drive shaft allows raising of an impeller above the bottom of the tank and/or allows for multiple impellers to be used. A mixing system of a vessel can be disposable or intended for a single use, along with the container in some cases. Various methods for mixing fluids can be implemented in the container. For instance, impellers based on magnetic actuation, sparging, and/or air-lift can be used. Direct shaft-drive mixers that are sealed and not magnetically coupled can also be used. Additionally or alternatively, a mixing system can include an impeller with varying impeller blade configurations.

Many disclosed examples include the use of collapsible bags, liners, or flexible containers. In addition, an embodiment of the invention can include systems utilizing non-collapsible bags, rigid containers, semi-flexible containers and other configurations involving liquid containment.

The collapsible bag can be made out of inherently flexible materials, such as many plastics, or can be made out of what are normally considered rigid materials such as glass or certain metals, but having a thickness or other physical properties rendering the container as a whole unable to maintain its shape or structural integrity when subjected to the internal pressures expected during operation without the benefit of a separate support structure. In some embodiments, collapsible bags include a combination of flexible materials and substantially rigid materials such as a rigid polymer, metal, or glass. For example, the collapsible bag, liner or other container can include rigid components such as connections, ports, supports for a mixing and/or antifoaming system.

In some embodiments, a rigid container or a collapsible bag comprises a polymeric material, for example, as a bulk material. Polymeric materials, such as the ones described herein, can be selected or formulated to have suitable physical and mechanical characteristics, for example, by tailoring the amounts of components of polymer blends to adjust the degree of any expected cross-linking. For instance, those of ordinary skill in the art can choose suitable polymers for use in containers based on factors such as the polymer's thermal conductivity, compatibility with certain processing techniques, compatibility with thermally-conductive materials, compatibility with any materials, such as cells, nutrients, solvents, contained in the container, and compatibility with sterilizations or other treatments or pre-treatments associated with performing a reaction inside the container.

In some embodiments, a collapsible bag is formed of a suitable flexible material, such as a homopolymer or a copolymer. The flexible material can be one that is USP Class VI certified, for example, silicone, polycarbonate, polyethylene, and polypropylene. Non-limiting examples of flexible materials include polymers such as polyethylene (for example, linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. Portions of the flexible container can comprise a substantially rigid material such as a rigid polymer, for example, high density polyethylene, metal, or glass. Substantially rigid materials can be utilized in areas for supporting fittings, for example.

In other embodiments, the container is a substantially rigid material. Optionally, all or portions of the container can be optically transparent to allow viewing of contents inside the container. The materials or combination of materials used to form the container can be chosen based on one or more properties such as flexibility, puncture strength, tensile strength, liquid and gas permeability, opacity, and adaptability to certain processes such as blow molding for forming seamless collapsible bags. The container can be single use or disposable in some cases.

The container can have any suitable thickness for holding a liquid and can be designed to have a certain resistance to puncturing during operation or while being handled. The thickness of a material such as a container wall is often specified in "mils." A mil is a unit of length equal to one thousandth ($10^{-3}$) of an inch, which is equivalent to 0.0254 millimeter. The unit "millimeter" is abbreviated herein as "mm." For example, a thickness of the flexible wall portions of a collapsible bag suitable for use in an embodiment of the invention can be less than 10 mils (less than 0.254 mm), or from about 10 mils to about 100 mils (from about 0.254 mm to about 2.54 mm) or from about 15 mils to about 70 mils (from about 0.38 mm to about 1.78 mm), or from about 25 mils to about 50 mils (from about 0.64 mm to about 1.27 mm). In yet another example, the walls of a container can have a total thickness of about 250 mils.

In some embodiments, the container includes more than one layer of material that can be laminated together or otherwise attached to one another in order to impart certain properties to the container. For instance, one layer can be formed of a material that is substantially oxygen impermeable. Another layer can be formed of a material to impart strength to the container. Yet another layer can be included to impart chemical resistance to a fluid that may be contained in the container. One or more layers of the container can include a thermally-conductive material to facilitate heat transfer to and from the interior of the container to an environment outside of the container, as described in more detail below.

A container, liner, or other article disclosed herein can be formed of any suitable combinations of layers. Non-limiting examples include an article comprising from 1 layer to about 5 layers of the same or different materials. Each layer can have a thickness of, for example, from about 3 mils to about 200 mils (from about 0.076 mm to about 5.08 mm), or combinations thereof.

Components that are integrated with collapsible bags or other containers can be formed in any suitable material, that may be the same or different from the material of the bag or container. In one embodiment, a container is formed in a first polymer and a component is formed in a second polymer that is different, for example, in composition, molecular weight, or chemical structure, from the first polymer. Those of ordinary skill in the art will be familiar with material processing techniques and will be able to use such techniques in the methods described herein to choose suitable materials and combinations of materials.

A rigid container or a collapsible bag suitable for use in an embodiment of the invention can have any size for containing a liquid. For example, the container can have a volume from about 0.1 liter to about 10,000 liters (from about 100 cubic centimeters to about $1 \times 10^7$ cubic centimeters.) The term "cubic centimeter" will be abbreviated herein as "$cm^3$." In other non-limiting examples, the container can have a volume from about 5 liters to about 5,000 liters (from about 5,000 $cm^3$ to about $5 \times 10^6$ $cm^3$), or from about 40 liters to about 1,000 liters (from about $4 \times 10^4$ $cm^3$ to about $1 \times 10^6$ $cm^3$). Volumes greater than 10,000 liters ($1 \times 10^7$ $cm^3$) are also possible. The suitable volumes can depend on the particular use of the container. For example, a collapsible bag used as a heat exchanger can have a smaller volume than a collapsible bag used to hold and store a large amount of fluid.

If a collapsible bag is used, it can be substantially deflated prior to being filled with a liquid, and can begin to inflate as it is filled with liquid. In other embodiments, the invention can include open container systems.

Many existing collapsible bags are constructed from two sheets of a plastic material joined by thermal or chemical bonding to form a container having two longitudinal seams. The open ends of the sheets are then sealed using known techniques, and access apertures are formed through the container wall. In some embodiments, seamless collapsible bags can be made specifically to fit a particular reusable support structure having a unique shape and configuration. Substantially perfect-fitting collapsible bags can be used, for example, as part of a bioreactor system or a biochemical or chemical reaction system. Seamless rigid or semi-rigid containers can also be beneficial in some instances.

Additional description of seamless containers can be found in U.S. patent application Ser. No. 11/818,901, filed Jun. 15, 2007, entitled, "Gas Delivery Configurations, Foam Control Systems, and Bag Molding Methods and Articles for Collapsible Bag Vessels and Bioreactors," by G. Hodge, et al., published as US2008/0068920 A1 on Mar. 20, 2008, the entire teachings of which are incorporated herein by reference.

The invention is described in more detail in the following examples, which are provided by way of illustration and are not intended to limit the invention in any way. In one embodiment, a vessel configured to contain a volume of liquid is a part of a bioreactor system. Turning now to the drawings, the schematic diagram of FIG. 1 depicts vessel 10, which includes a reusable support structure 14. An example of the support structure 14 is a stainless steel tank or vessel—that surrounds and contains a container 18. In some embodiments, the container 18 is configured as a collapsible bag or liner, for example, a polymeric bag, and can optionally include tubing, a magnetic drive pump, and/or a foam breaker. In other embodiments, the container 18 is made of a substantially rigid material. The container 18 can be disposable, and can be configured to be easily removable from the support structure, or configured to be irreversibly connected to the support structure.

If a collapsible bag is used as container 18, it can be constructed and arranged for containing a liquid 22, which can contain reactants, media, or other components necessary for carrying out a desired process such as a chemical, biochemical or biological reaction. The collapsible bag can also be configured such that liquid 22 remains substantially in contact only with the collapsible bag during use and not in contact with support structure 14. In such embodiments, the collapsible bag can be disposable and used for a single reaction or a single series of reactions, after which the bag is discarded. Because the liquid in the collapsible bag in such embodiments does not come into contact with the support structure 14, the support structure 14 can be reused without cleaning. After a reaction takes place in container 18, the container 18 can be removed from the reusable support structure 14 and replaced by a second disposable container. A second reaction can be carried out in the second container without having to clean either the first container 18 or the reusable support structure 14. If any liquid 22 does come into contact with the reusable support structure due to leakage from the bag, in certain embodiments, one or more leak detection systems that are associated with vessel 10 detect the leak and notify the user so that appropriate measures can be taken.

Also shown in FIG. 1 are an optional inlet port 42 and optional outlet port 46, which can be formed in the container 18 or reusable support structure 14, and can facilitate more convenient introduction and removal of a liquid 14 or gas from the container 18. The container 18 can have any suitable number of inlet ports 42 and any suitable number of outlet ports 46. For example, a plurality of inlet ports 42 can be used to provide different gas compositions via a plurality of spargers 47, or to allow separation of gases prior to their introduction into the container 18. These ports can be positioned in any suitable location with respect to container 18. For instance, for certain vessels including spargers 47, the container 18 can include one or more gas inlet ports located at a bottom portion of the container 18. Tubing can be connected to the inlet and outlet ports 42 and 46 to form delivery and harvest lines, respectively, for introducing and removing liquid from the container 18. Optionally, the container 18 or support structure 14 can include a utility tower 50, which facilitates interconnection of one or more devices internal to the container 18 or support structure 14 with one or more pumps, controllers, or electronics, such as sensor electronics, electronic interfaces, and pressurized gas controllers or other devices. Such devices can be controlled using a control system 34. The control system 34 can also be used to send signals to and receive signals from a leak detection system and a wrinkle removal system.

For systems including multiple spargers 47, control system 34 can be operatively associated with each of the spargers 47 and configured to operate the spargers 47 independently of each other. This can allow control of multiple gases being introduced into the container 18.

In general, as used herein, a component of an inventive system that is "operatively associated with" one or more other components indicates that such components are directly connected to each other, in direct physical contact with each other without being connected or attached to each other, or are not directly connected to each other or in contact with each other, but are interconnected mechanically, electrically, fluidically, or remotely via electromagnetic signals, so as to cause or enable the components so associated to perform their intended functionality.

The vessel 10 can optionally include a mixing system such as an impeller 51, which can be rotated about an axis using a motor 52 that can be external to the container 18. In some embodiments, as described in more detail below, the impeller 51 and motor 52 are magnetically coupled. The mixing system can be controlled by control system 34. Mixing systems are described in further detail below.

Additionally or alternatively, the vessel 10 can include an antifoaming system such as a mechanical antifoaming device. As shown in the embodiment illustrated in FIG. 1, an antifoaming device can include, for example, an impeller 61 that can be rotated magnetically using a motor 62, which can be external to the container 18. The impeller 61 can be used to collapse a foam contained in a head space 63 of the container 18. In some embodiments, the antifoaming system is in electrical communication with a sensor 43, for example, a foam sensor, via control system 34. The sensor 43 can determine, for instance, the level or amount of foam in the head space 63 or the pressure in the container 18. The determination by the sensor 43 can trigger regulation or control of the antifoaming system. In other embodiments, the antifoaming system is operated independently of any sensors.

The support structure 14 and/or the container 18 can also include, in some embodiments, one or more ports 54 that can be used for sampling, determining and/or analyzing conditions such as pH or the amount of dissolved gases in the liquid 22 or for other purposes. The support structure 14 can also include one or more site windows 60 for viewing a level of liquid 22 within the container 18. One or more connections 64 can be positioned at a top portion of the container 18 or at any other suitable location. Connections 64 can include openings, tubes, and/or valves for adding or withdrawing liquids, gases, and the like from the container 18, each of which can optionally include a flow sensor and/or filter (not shown). The support structure 14 can further include a plurality of legs 66, optionally with wheels 68 for facilitating transport of the vessel 10.

As will be explained in further detail below, the vessels or reactor systems of the present invention are equipped with a heat exchange module, which can include a body configured to be disposed in the reactor system having an inner replaceable reactant container, the body further including at least one thermally conductive surface adapted to contact the inner container to facilitate heat transfer, and a heat exchanger disposed within the module body having a fluid circulation path through which a heat exchange fluid can be circulated.

It should be understood that not all of the features shown in FIG. 1 need be present in all embodiments of the invention and that the illustrated elements can be otherwise positioned or configured. Also, additional elements can be present in other embodiments, such as the elements described herein. In some embodiments, one or more components shown in FIG. 1 are configured to be a part of a bioreactor system 100, as illustrated in FIG. 2 and as described in more detail below.

Figure 2:
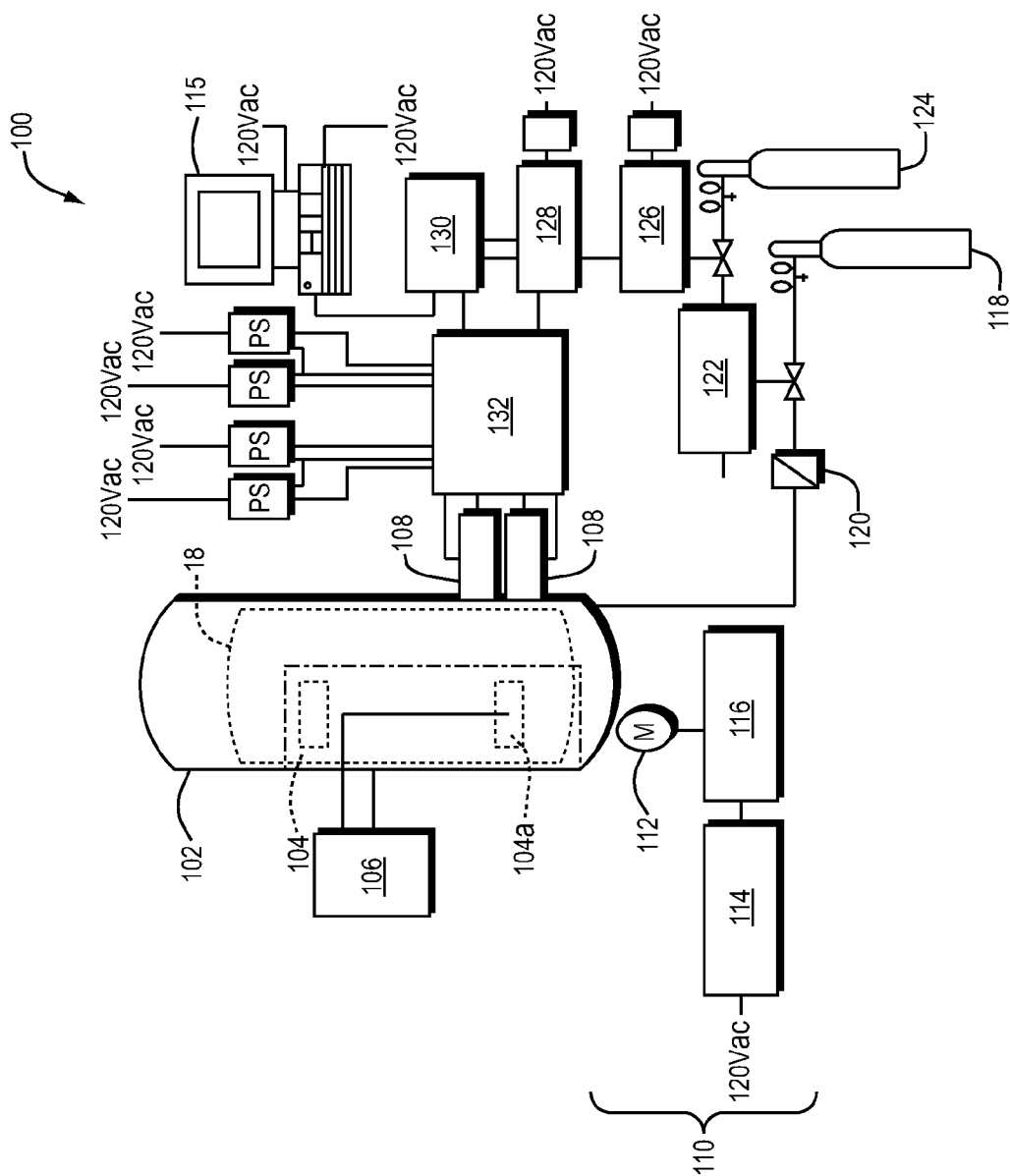
FIG. 2 is a schematic representation of a system for carrying out fluid manipulations including biological, chemical, and biochemical processes, according to another embodiment of the invention.

In some embodiments, a heat exchange system described herein is in fluid communication with one or more components of a bioreactor system, such as bioreactor system 100, as shown schematically in FIG. 2. For example, container 18 can be operatively associated with and/or in fluid communication with a temperature controller 106 which can comprise a heat exchanger 200 described in connection with FIGS. 3-18. In other embodiments, however, a closed loop water jacket, an electric heating blanket, a PELTIER heater or cooler, or other temperature control system known to those of ordinary skill in the art can also be used in combination with container 18.

In one embodiment of the invention, an intercooler can be used to provide cooling of the inlet sparge gas and/or head space gas before it enters the bioreactor. This use of an intercooler provides additional heat removal from the liquid in the bioreactor as the cooled gas passes through the bioreactor. It is well known that sweeping the headspace of a bioreactor with a gas such as air from an external supply can help remove carbon dioxide from the headspace and control the pH of the liquid in the bioreactor. Cooled air entering the head space will also increase condensation on the head space which will reduce moisture load on the exit air condenser. An example of a device suitable for use as an intercooler is described in International Application No. PCT/US2010/050859 filed on Sep. 30, 2010, published in English on Apr. 7, 2011 as WO/2011/041508, the entire teachings of which are incorporated herein by reference.

The temperature control system can also include a thermocouple and/or a resistance temperature detector for sensing a temperature of the contents inside the container 18. The thermocouple can be operatively connected to the temperature controller/heat exchanger to control temperature of the contents in the container 18. Optionally, as described herein, a thermally-conductive material can be associated with a surface of the container 18, for example, to provide a heat transfer surface 104, 104A in FIG. 2, or 804, 814 in FIGS. 19A and 19B, respectively, to overcome the insulating effect of the polymeric material used to form portions of the container 18.

In some cases, sensors 108 and/or probes can be connected to a sensor electronics module 132, the output of which can be sent to a terminal board 130 and/or a relay box 128. Various sensors and/or probes for controlling and/or monitoring one or more process parameters inside the container such as, for example, temperature, pressure, pH, dissolved oxygen (DO), dissolved carbon dioxide ($DCO_2$), mixing rate, and gas flow rate, can be used. The results of the sensing operations can be input into a computer or computer-implemented control system 115 for calculation and control of various parameters such as temperature and weight/volume measurements, and for display and user interface. Such a control system 115 can also include a combination of electronic, mechanical, and/or pneumatic systems to control heat, air, or liquid delivered to or withdrawn from the container 18 as required to stabilize or control the environmental parameters of the process operation. It should be appreciated that the control system 115 can perform other functions and is not limited to having any particular function or set of functions.

The one or more control systems 115 can be implemented in numerous ways, such as with dedicated hardware and/or firmware, using a processor that is programmed using microcode or software to perform the functions recited above or any suitable combination of the foregoing. A control system 115 can control one or more operations of a single reactor for a biological or chemical reaction, or of multiple reactors that are separate or interconnected. The embodiment depicted in FIG. 2 depicts a drive control system 110 comprising a drive motor 112 for the agitator/impeller system, the controller 114 for controlling drive, and the drive 116 for controlling the motor 112.

Each embodiment of a system described herein, for example, with reference to FIG. 2, and components thereof, can be implemented using any of a variety of technologies, including software, for example, C, C#, C++, Java, or a combination thereof; hardware, for example, one or more application-specific integrated circuits; firmware, for example, electrically-programmed memory; or any combination of the foregoing.

Various embodiments described herein can be implemented on one or more computer systems. These computer systems, can be, for example, general-purpose computers such as, for example, those based on INTEL® processors such as PENTIUM® or XSCALE® (INTEL Corporation, Inc.). It should be appreciated that one or more of any type of computer system can be used to implement various embodiments described herein. The computer system can include specially-programmed, special-purpose hardware, for example, an application-specific integrated circuit (ASIC). Various components can be implemented in software, hardware or firmware, or any combination thereof. Further, such methods, acts, systems, system elements and components thereof can be implemented as part of the computer system described above or as an independent component.

A vessel can also be connected to one or more sources of gases 118, 124 such as air, oxygen, carbon dioxide, nitrogen, ammonia, or mixtures thereof, in some embodiments. The gases can be compressed or can be pumped, for example. Such gases can be used, for example, to provide suitable growth or reaction conditions for producing a product inside the container 18. The gases can also be used to provide sparging to the contents inside the container, for mixing, or for other purposes.

In FIG. 2, the inlet gases from sources of gases 118 and 124 can optionally pass through filter 120 and/or a flow meter and/or valve 122, which can be controlled by controller system 115, prior to entering the container 18. Valve 122 can be a pneumatic actuator, actuated by, for example, compressed air, carbon dioxide, or other gas 124, which can be controlled by a solenoid valve 126. These solenoid valves 126 can be controlled by a relay 128 connected to terminal board 130, which is connected to the controller system 115. The terminal board can comprise, for example, a PCI terminal board, or a USB/parallel, or fire port terminal board of connection. In other embodiments, flush closing valves can be used for addition ports, harvest and sampling valves. Progressive tubing pinch valves that are able to meter flow accurately can also be used. In some cases, for example, for inlet ports, outlet ports, and sampling ports, the valves can be flush closing valves. The inlet gases can be connected to any suitable inlet of the vessel. In one embodiment, the inlet gases are associated with one or more spargers which can be controlled independently, as described in more detail below.

As shown in the exemplary embodiment illustrated in FIG. 2, the container 18 and support structure 14 illustrated in FIG. 1 can be operatively associated with a variety of components as part of an overall bioreactor system 100. Accordingly, in FIG. 2, the container 18 and/or support structure 102 can include several fittings to facilitate connection to functional components such as filters, sensors, and mixers, as well as connections to lines for providing reagents such as liquid media, gases, and the like. The container 18 and the fittings can be sterilized prior to use so as to provide a "sterile envelope" protecting the contents inside the container 18 from airborne contaminants outside. In some embodiments, the contents inside the container 18 do not contact the reusable support structure 102 and, therefore, the reusable support structure 102 can be reused after carrying out a particular chemical or biological reaction without being sterilized, while the container 18 and/or fittings connected to the container 18 can be discarded. In other embodiments, the container, fittings, and/or reusable support structure 102 can be reused (for example, after cleaning and sterilization).

As used herein, the term "temperature-controlling surface" has the same meaning as "heat transfer surface." A temperature-controlling surface can be in contact with one or more exterior or interior surface portions of a collapsible bag or tubing. A temperature-controlling surface can comprise a thermally conductive surface formed of a thermally conductive material, such as, e.g., a plurality of particles 804, 814, FIGS. 19A, 19B, respectively. The particles 804, 814 are embedded in a surface of a flexible polymeric tubing 802 in a section of a tubing 800, or in a surface of a film 812 in a section of a flexible bag 810, respectively. The tubing 802 and the bag 810 can be single-walled or double-walled, and in the case of a double-wall, the thermally conductive material can be embedded in at least one of the inner or the outer wall. A temperature-controlling surface can comprise a thermally conductive plate comprising channels for allowing fluid to flow therethrough, channels for allowing fluid to flow therethrough wherein the channels are not associated with a plate, and combinations of the foregoing.

The temperature of the fluid flowing in the collapsible bag 18 can be changed, in one embodiment, by associating one or more surfaces of the collapsible bag with a heat transfer surface, for the purpose of promoting transfer of heat to and/or from the collapsible bag 18. In some embodiments, a system of the invention includes a heat exchange module adapted to contact the bag 18.

To enhance heat conduction, one or more surfaces of the collapsible bag can be associated with a heat transfer surface, for example, a thermally-conductive material. For instance, in one embodiment, the material used to form the collapsible bag can have thermally-conductive particles embedded therein. In certain embodiments, an exterior surface portion of the collapsible bag is also in contact with a temperature controlling surface comprising a thermally conductive material, such as a thermally conductive surface disposed on a heat exchange module.

In some cases, the rate of heat exchange is limited below desirable or optimal levels by the material used to form a heat transfer surface or container. For instance, systems involving the use of disposable liners in the form of collapsible bags are generally made of low thermally-conductive materials such as polyethylene, polytetrafluoroethylene (PTFE), or ethylene vinyl acetate. To address this problem, surfaces described herein, such as collapsible bags or rigid containers, can include in certain embodiments one or more thermally-conductive material(s) associated therewith. In one embodiment, a surface comprises a thermally-conductive material embedded in at least a portion of the surface. Additionally or alternatively, the thermally-conductive material can line a wall of the container. For instance, the thermally-conductive material and the wall of the container can form a laminate structure.

Advantageously, a heat exchanger module can be utilized in systems experiencing said undesirable heat transfer characteristics. The heat exchanger module can be formed and configured such that a thermally-conductive material is adapted to conduct heat away from an interior of the container to an environment outside of the container, or to conduct heat into the container from an environment outside of the container. In embodiments in which the container is supported by a reusable support structure, for example, thermally-conductive plates or a stainless steel tank, heat conduction away from or into the container can be facilitated by the heat exchange module coupled to the support structure. For instance, heat from the contents inside the container can be dissipated, via the thermally-conductive material of the container, to the support structure which can also be thermally-conductive.

In some embodiments, the thermally-conductive material is in the form of a plurality of particles. The particles can be in the form of nanoparticles, microparticles, powders, and the like. The thermally-conductive material can also be in the form of nanotubes, nanowires, nanorods, fibers, meshes, or other entities. The thermally-conductive material can be embedded in the material used to form the container, for example, such that all or a portion of each entity is enveloped or enclosed by the material used to form the container.

In some embodiments, an embedded thermally-conductive material is substantially uniformly dispersed throughout a bulk portion of a material used to form a container. "Substantially uniformly dispersed," in this context, means that, upon viewing a cross-sectional portion of any such material, where the cross-section comprises the average makeup of a number of random cross-sectional positions of the material, investigation of the material at a size specificity, for example, on the order of grains, or atoms, reveals essentially uniform dispersion of the thermally-conductive material in the bulk material. A photomicrograph, scanning electron micrograph, or other similar microscale or nanoscale investigative process may reveal essentially uniform distribution.

It should be understood that in other embodiments, a thermally-conductive material is not substantially uniformly dispersed throughout a bulk portion of the material used to form a heat transfer surface. For example, a gradient of particles can be formed across a cross-section of the heat transfer surface. For example, the thermally-conductive material can be configured such that one portion of the heat transfer surface includes a thermally-conducive material and another, adjacent portion of the container or heat exchange module also comprises the thermally-conductive material. Alternatively, the thermally-conductive material can be present as strips, wires, or can have other configurations such that one portion of the heat transfer surface includes a thermally-conducive material and another, adjacent portion of the container or heat exchange module does not comprise a thermally-conductive material.

The thermally-conductive material can in certain embodiments be encapsulated between two polymeric sheets. Alternating layers of thermally-conductive material and polymeric layers are also possible. Alternatively, in some embodiments, an outer surface of the container or liner can include a layer of thermally-conductive material, while an inner surface of the container or liner does not include the thermally-conductive material. This configuration can allow heat to be conducted away from (or into) the contents of the container or liner, while avoiding or limiting any reactivity between the contents of the container or liner and the thermally-conductive material. For example, silver has a high thermal conductivity and can be used as a thermally-conductive material, but is known to have antimicrobial effects. By positioning the silver at an outer surface of the container (or embedded between two polymer layers), but not in contact with any contents inside the container, heat conduction of the container can be enhanced without adversely affecting the contents inside the container (for example, cells, proteins, etc.).

The thermally-conductive material may have any suitable size or dimension. The size of the thermally-conductive entities can be chosen, for example, to achieve a certain dispersion, for example, a gradient or a substantially uniformly dispersion, within the bulk material used to form the heat transfer surface, to prevent protrusion of the entity through a portion of the container, or to have a certain surface area or thermally conductive material to volume ratio. For example, the thermally-conductive material may have at least one cross-sectional dimension less than 500 microns, or in another embodiment less than 1 nanometer.

Any suitable thermally conducting material can be used as a thermally-conductive material in an embodiment of the invention. The thermally-conductive material can be chosen based on factors such as its thermal conductivity, particle size, magnetic properties, compatibility with certain processing techniques, for example, ability to be deposited by certain deposition techniques, compatibility with the bulk material used to form the container, compatibility with any materials contained in the container, compatibility with any treatments or pre-treatments associated with performing a reaction inside the container, as well as other factors.

In one set of embodiments, the thermally-conductive material comprises a metal. In other cases, the thermally-conductive material comprises a semiconductor. Materials potentially suitable for use as thermally-conductive materials include, for example, an element in any of Groups 1-17 of the Periodic Table. Typical examples include a Group 2-14 element, or a Group 2, 10, 11, 12, 13, 14, 15 element. Non-limiting examples of potentially suitable elements from Group 2 of the Periodic Table include magnesium and barium; from Group 10 include nickel, palladium, or platinum; from Group 11 include copper, silver, or gold; from Group 12 include zinc; from Group 13 include boron, aluminum, and gallium; from Group 14 include carbon, silicon, germanium, tin, or lead. In some cases, the thermally-conductive material is aluminum, copper, iron, or tin.

The thermally-conductive material can comprise one or more metals. Similarly, where the thermally-conductive material comprises a semiconductor, one or more semiconducting materials can be used. Additionally, alloys can be used, and a mixture of metals and semiconductors can be used. That is, the thermally-conductive material can be a single metal, a single semiconductor, or one or more metals or one or more semiconductors mixed. Non-limiting examples of suitable metals are listed above, and suitable components of semiconductors are listed above. Those of ordinary skill in the art are well aware of semiconductors that can be formed from one or more of the elements listed above, or other elements.

In certain cases, the thermally-conductive material is a nonmetal. For example, the thermally-conductive material can comprise carbon. The thermally-conductive material can be in the form of a conductive polymer, for instance. Non-limiting examples of conductive polymers include polypyrroles, polyanilines, polyphenylenes, polythiophenes, and polyacetylenes.

Those of ordinary skill in the art can easily select, without undue burden or undue experimentation, from materials described above or other materials known in the field, suitable metals, semiconductors, and/or nonmetals. The teachings described herein also enable those of skill in the relevant art to screen materials for suitable use in connection with embodiments described herein. Optionally, thermally-conductive materials can be coated or treated to enhance certain chemical or physical properties of the materials. For example, the surfaces of the thermally-conductive materials can be treated with a surfactant, an oxide or any other suitable material, to make the materials more hydrophilic, more hydrophobic, less reactive, have a certain pH, and so forth. These and other processes can allow the thermally-conductive materials to be more compatible with the material used to form the container and/or with certain processing techniques. For example, treatment of the thermally-conductive material can allow it to adhere to the material used to form the container to a desired degree, be more soluble in a particular solvent, or be more dispersible.

The components of FIGS. 1 and 2 can be utilized in combination with a heat exchange module described herein. The heat exchange module can facilitate heat transfer with the inner container and can be used to change the temperature of a fluid to varying degrees. For instance, the temperature of a fluid can be varied by at least 2° C., at least 5° C., at least 10° C., at least 15° C., at least 20° C., or at least 30° C.

Figure 3:
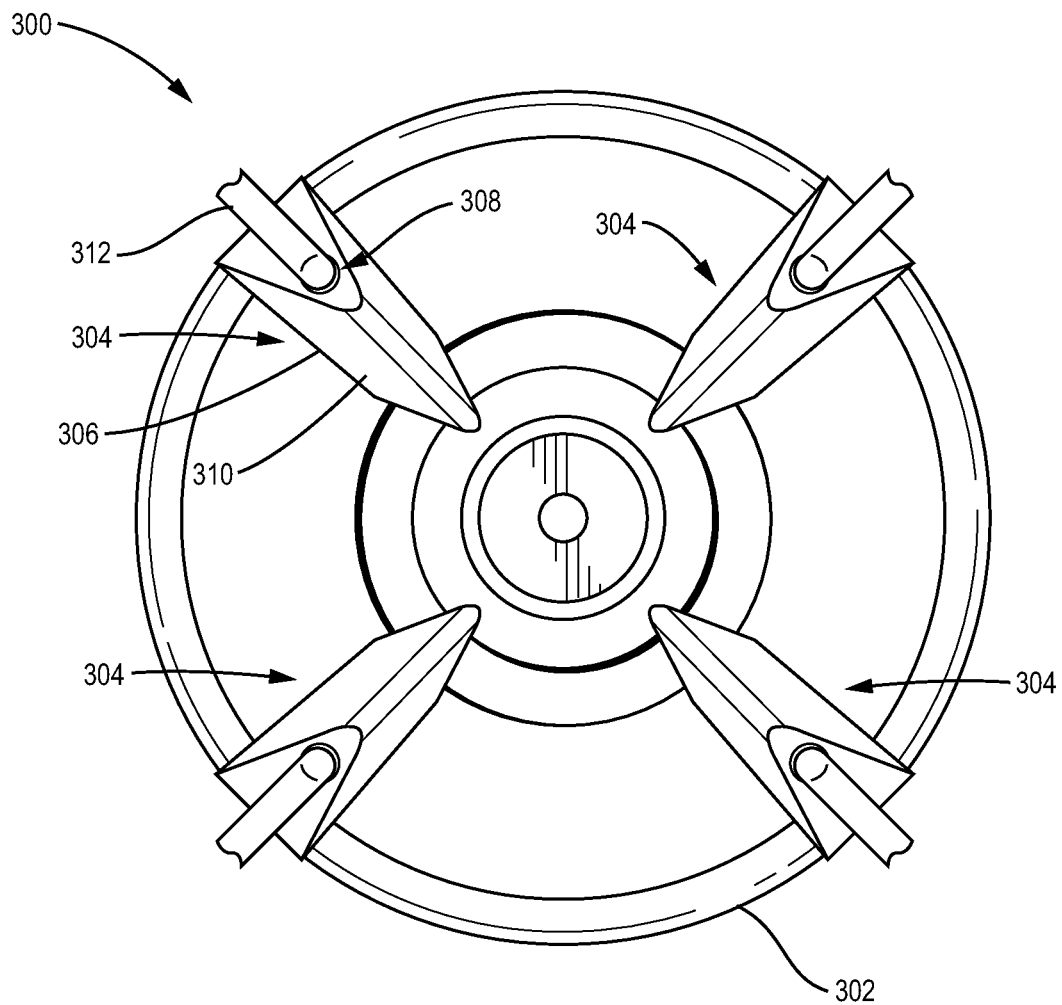
FIG. 3 is a top view of an exemplary embodiment of a reactor system having at least one heat exchanger module according to the invention.

As shown in a top view of an exemplary embodiment in FIG. 3, the reactor system 300 can include an outer support structure, also referred to herein as a tank or a vessel 302, an inner replaceable or single-use container such as a flexible bag (not shown), and at least one heat exchange module 304 adapted to contact the inner reactor container (not shown). The heat exchange module 304 can comprise a body 306 and a heat exchanger 308 disposed within the body 306. The body 306 can comprise at least one thermally conductive surface 310 adapted to contact the inner container to facilitate heat transfer. In an exemplary embodiment, the at least one thermally conductive surface 310 can be adapted to contact a portion of a collapsible bag 18 shown in FIG. 1. As can be seen in FIG. 3, the at least one heat exchange module 304 can be in fluid communication with a heating or cooling fluid source 312, also referred to herein as a temperature control fluid, and can be disposed between a support structure 302 and an interior of the reactor system.

A reactor system can be fitted with a varying number of heat exchange modules. One non-limiting embodiment, shown in FIG. 3, includes four (4) heat exchange modules 304. In other embodiments, the desired level of temperature regulation can be achieved with one (1) heat exchange module, but a system can include any number of modules. One skilled in the art will recognize the adaptability of the system to desired operating parameters. The heat exchange module 304 can optionally be attached or coupled to the vessel by means of a hook and removable from the reactor system. The inner container or flexible bag and the heat exchanger module 304 can be removed after a first manipulation process, and replaced with new containers or heat exchange modules 304 so as to maintain the sterile environment for the second process without the need for washing any components of the system.

Wand Embodiment

Figure 4A:
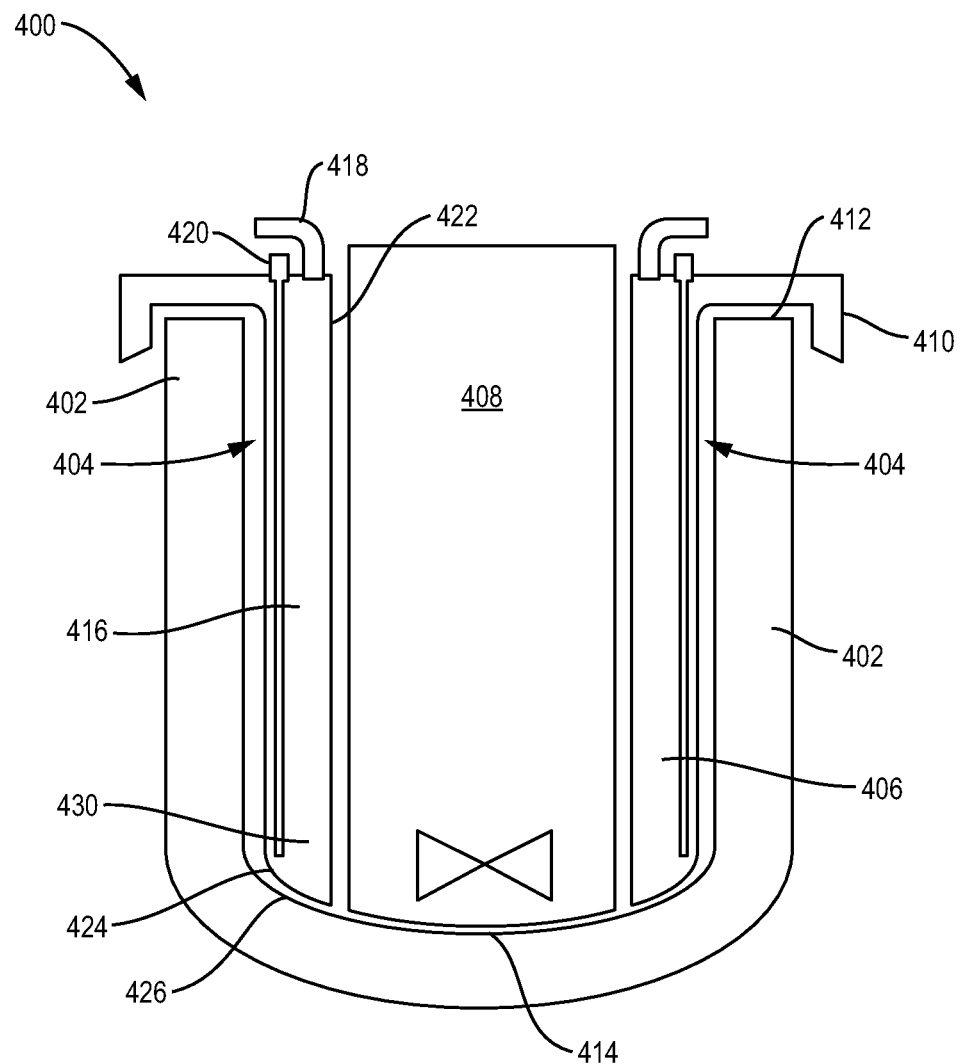
FIG. 4A is a cross-sectional side view of an exemplary embodiment having at least one heat exchanger module according to the invention.

FIG. 4A is a cross-sectional side view of an exemplary reactor system 400 having at least one heat exchanger module 404 wherein the heat exchange module 404 comprises a wand-like body 406, the bottom portion 424 of which is configured to conform to the shape of the support structure 402. The body 406 can be disposed vertically between an outer support structure 402 and the interior of the inner container 408, as shown, using a coupler 410 and can be elongate to extend at least a substantial portion of the distance between the top 412 and bottom 414 of the support structure 402.

Disposed within the body 406, a heat exchanger 416 can produce a fluid flow path for a temperature control fluid to circulate through the heat exchange module 404. The heat exchanger can be in fluid communication with a temperature control fluid source and have an inlet 420 and an outlet 418. Furthermore, the body 406 can include a thermally conductive surface 422 that is in thermal communication with the heat exchanger 416. The thermally conductive surface 422 can be adapted to contact the surface of the inner container 408 so as to facilitate heat transfer between the heat exchange module 404 and the inner container 408. The thermally conductive surface 422 can be formed of known conductive materials as described above. The end 424 of the wand-like body 404 is adapted to fit the curvature of the bottom of the outer support structure 414, 426.

Figure 4B:
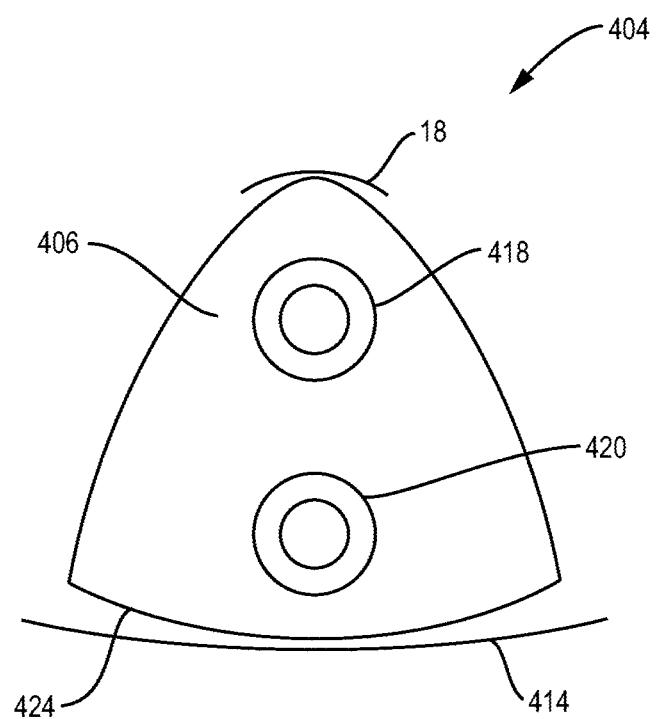
FIG. 4B is a cross-sectional, top view of a heat exchanger or cooling wand disposed within a module body and configured to provide a fluid circulation path.

FIG. 4B is a cross-sectional, top view of a heat exchanger or cooling wand 404 disposed within a module body 406 and configured to provide a fluid circulation path. A liquid coolant supply or heat exchange fluid enters the elongate coolant supply dip tube 420, which extends substantially to the bottom of the cooling wand body 406, flows out of the opening at the bottom of the supply tube 420, across the inside bottom area of the cooling wand body and upwards to the outlet or outlet tube 418. As the heat exchange fluid flows upwards along the side of the cooling wand body 406 adjacent the bag 408, as shown in FIG. 4A and bag 18 as shown in FIG. 4B, the fluid carries away some of the heat generated in the bioreactor bag. FIG. 4B also shows optional curved back 424 of the cooling wand, the curvature conforming to the round support vessel wall 414.

Figure 5:
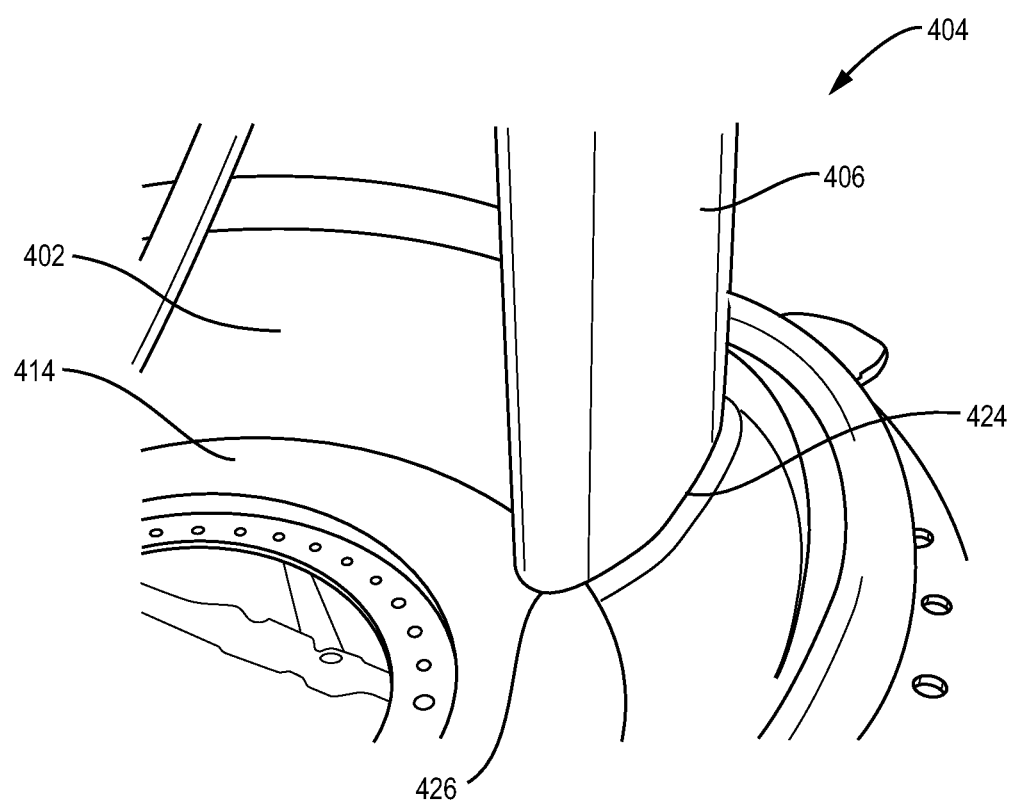
FIG. 5 is a partial perspective view of an embodiment of a heat exchanger module according to the invention wherein the module body has a surface configured to conform to a shape of an outer support structure and wherein the heat exchanger reaches to the bottom of the reactor vessel.

FIG. 5 is a partial perspective view of an embodiment of a heat exchanger module 404 wherein the wand-like body 406 has a surface 424 at its bottom tip configured to conform to a shape of the outer support structure 402, 414. By specifically contouring the body 406 to conform to the support structure 402, pinching and damage to the inner container/flexible bag 18 (in FIG. 4B) is avoided upon inflation of the bag with fluid.

Figure 6A:
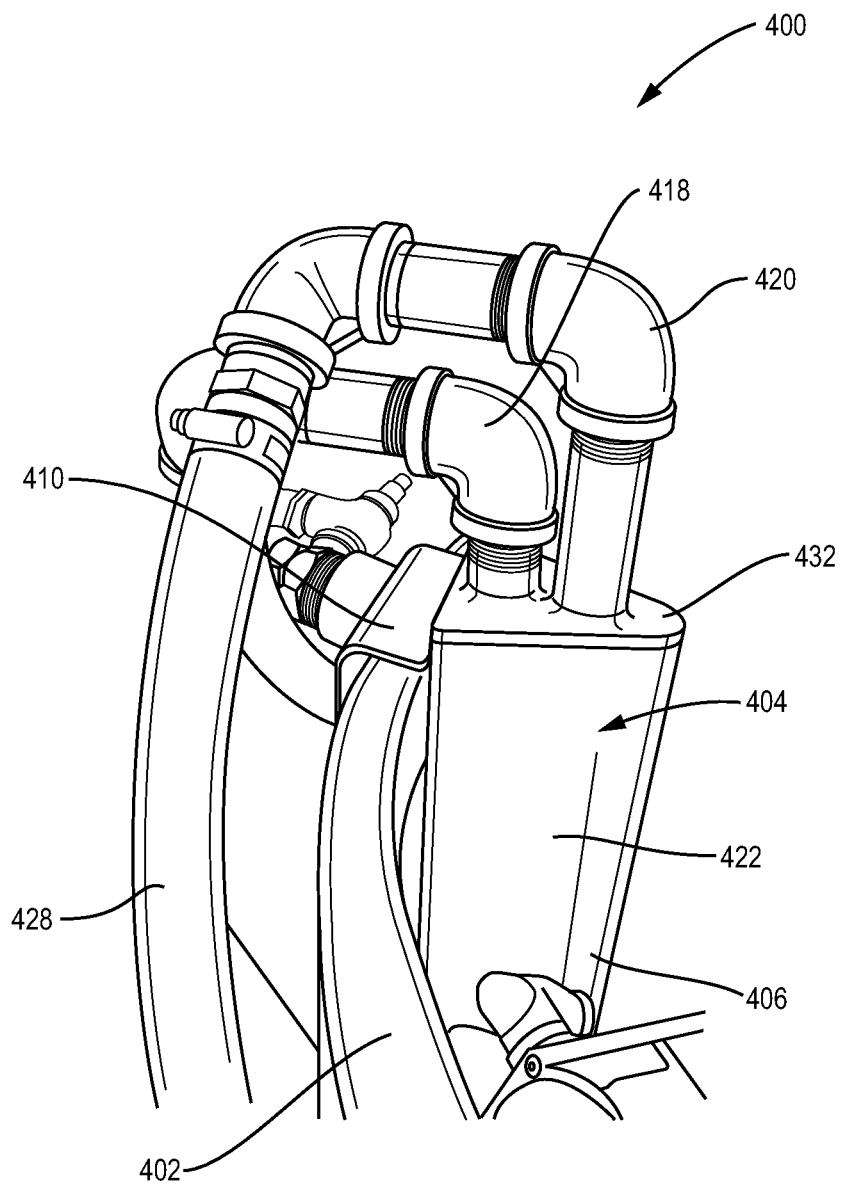
FIG. 6A is a partial perspective view of the heat exchanger module of FIG. 4A in a coupled position with the heat exchange module inserted into the reactor system.

In FIG. 6A, another partial perspective view of the heat exchanger module 404 is depicted in a coupled position with the heat exchanger module 404 inserted into the reactor system 400. In this exemplary embodiment, the body 406 is coupled to the outer support structure 402 via the coupler 410. Here the coupler 410 is a bracket, or hanger flange, and is designed to allow easy removal of the heat exchange module 404 from the system 400. The coupler 410 can be any type of coupler known in the art, such as a hanger flanges, bolt-type fasteners, cable ties, tongue-in-groove, weld, or any other suitable coupler. Removal of the heat exchange module 404 from the system 400 can be desirable for a variety of reasons, such as, but not limited to, cleaning.

Figure 6B:
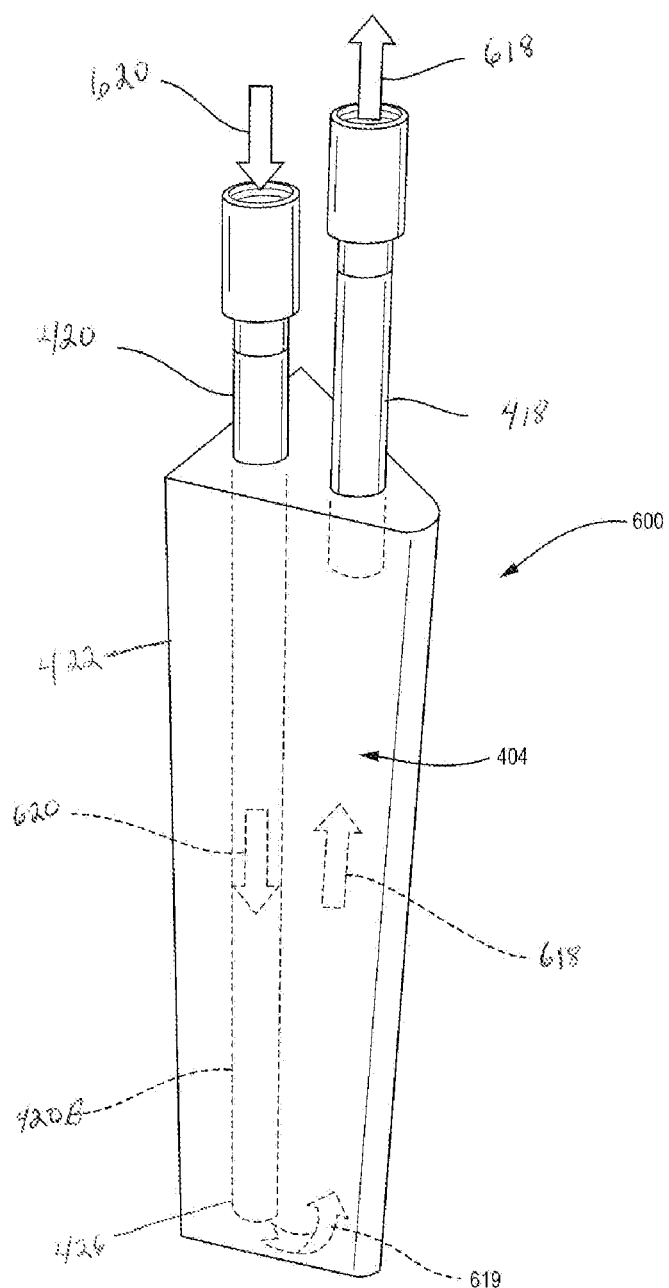
FIG. 6B is a perspective view of a heat exchange module showing the fluid circulation path.

FIG. 6B is a perspective view of a heat exchange module 600 in fluid communication with a temperature control fluid source 620. This exemplary heat exchange module 600 includes a fluid circulation path 620, 619, 618 through the module body 404. In an embodiment, a temperature controlling fluid enters the heat exchange module 600 through an inlet 420. In this embodiment the inlet 420 is connected to a temperature control fluid supply dip tube 420B that extends a substantial length of the body 404, carrying the temperature control fluid to an end 426 of the body 404. After exiting the supply dip tube 430, the temperature control fluid circulates through the heat exchanger portion 620, 619, 618 of the module body 404, forming a fluid flow path from the opening 420 of the supply dip tube 420B to an outlet tube 418 at an opposite end of the body 404. The heat exchanger portion, or the entire body 404, can be water and pressure tight permitting the temperature control fluid to fill the entire heat exchanger 416. By allowing the temperature control fluid to fill the entire body 404, the temperature of the thermally conductive surface 422 of the body 404 can be efficiently regulated. Alternatively, the body 404 can include any known heat exchanger materials, such as radiator plates, fluid coils or serpentine pipes, or other metal-to-metal conduction transfer elements.

Integral Baffle Embodiment

In some embodiments, the heat exchange module can be formed in the wall of the vessel or support structure providing a temperature regulating jacket to the inner container. As before, in these embodiments, a protrusion can extend into the interior of the support vessel, such that when the flexible container is inserted into the support structure vessel, the fluid inside the flexible container is both baffled and temperature regulated. By baffling the inner container, mixing within the container can be improved. This integral system provides physical support for the flexible container, temperature regulation of the reactor system, and can provide increased mixing. This integral cooling baffle support structure can be in the form of a vessel, integral liner, a flat plate system, or any other integral configuration.

Figure 7:
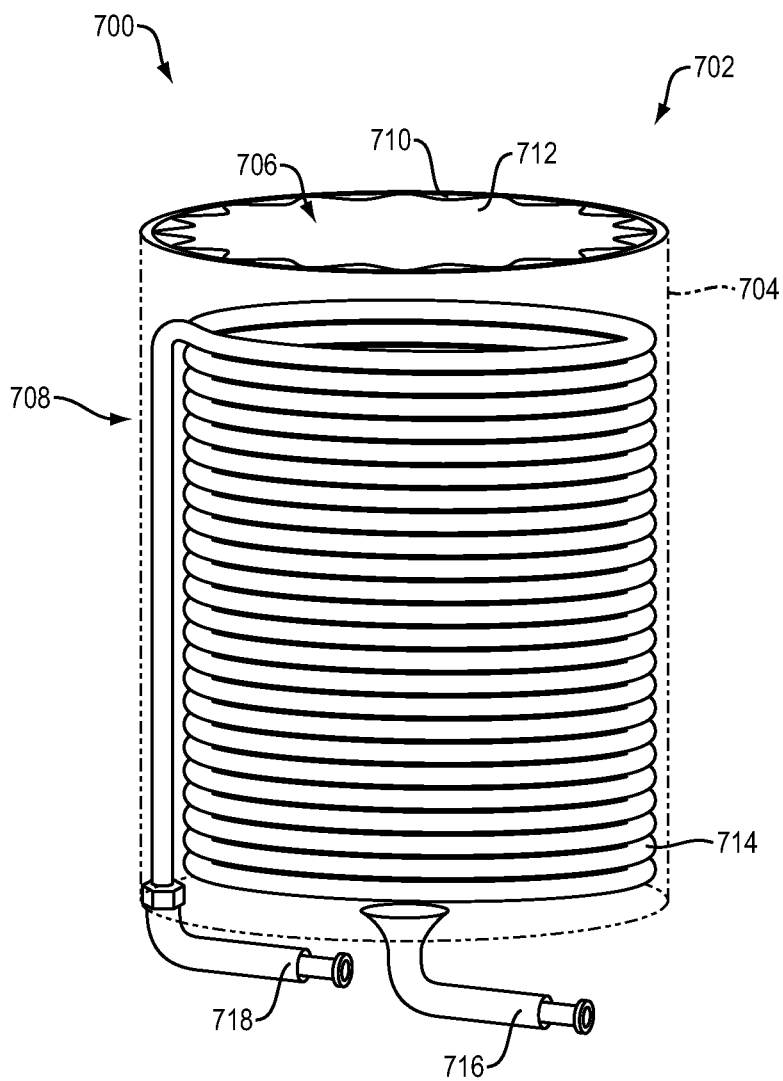
FIG. 7 is a perspective view of another exemplary embodiment of a heat exchange module for use in a reactor system according to the invention.

FIG. 7 is a perspective view of another exemplary embodiment of a heat exchange module 702 for use in a reactor system 700 wherein the heat exchange module 702 is integrally formed in the outer support structure 704. In this exemplary embodiment the reactor system 700 comprises an outer support structure 704 (shown in phantom) and a heat exchange module 702 wherein the heat exchange module 702 is integrally formed with the outer support structure 704 and comprises a body 706 and a heat exchanger 708. The heat exchange module 702 includes a body 706 having a baffle structure 710 presenting a plurality of thermally conductive surfaces 712. The baffle structure 710 is adapted to contact the inner container (not shown) as it is disposed on an interior surface of the support structure 704. In this embodiment, the heat exchange module 702 further includes a coiled fluid flow path 714 disposed concentrically around the outer support structure. The path 714 has an inlet 716 and an outlet 718 through which temperature control fluid is circulated.

Figure 8:
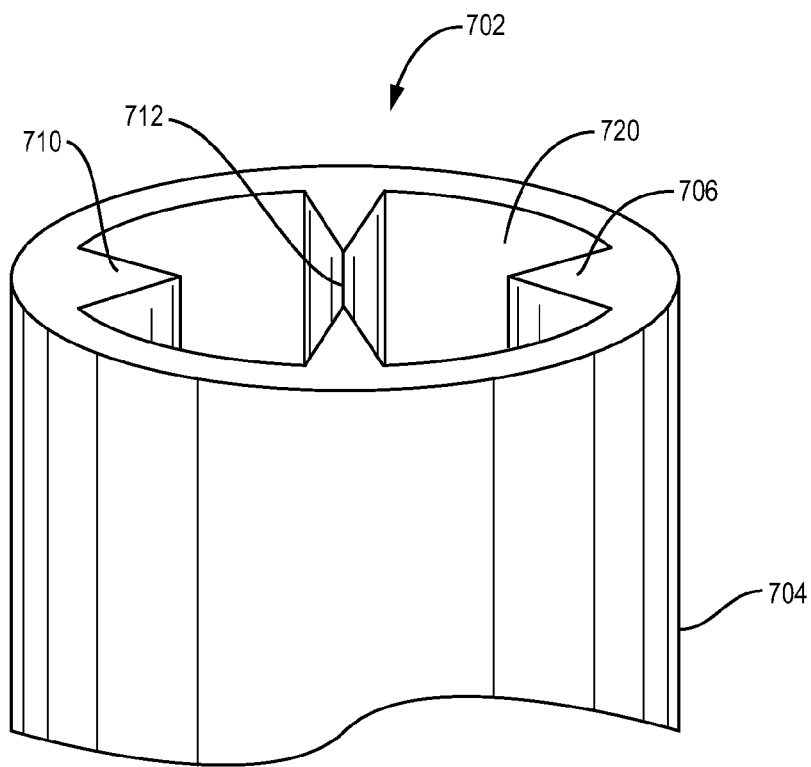
FIG. 8 is a partial perspective view of an exemplary heat exchange module that is incorporated into an outer support structure.

FIG. 8 is partial perspective view of an exemplary heat exchange module 702 incorporated into an outer support structure 704, e.g., such as the support structure shown in phantom in FIG. 7 wherein the baffle structures 710 form triangular protrusions aligned vertically along the support structure 702. The baffle structure 710 can alternatively be of any geometric shape, for instance, circular or rectangular. In some embodiments, the baffles 710 can also be hollow allowing temperature control fluid to flow throughout. The heat exchange module 702 is formed integrally with the outer support structure 704 and the heat exchange module 702 comprises a body 706 and a heat exchanger disposed within said body, e.g., as shown in FIG. 7. Here, the body 706 includes a thermally conductive surface 712 that can be disposed on the baffles 710 or the inner surface 720 between each baffle. The body includes a fluid circulation path through the space between the inner surface 720 and the outer support structure 704.

Figure 9:
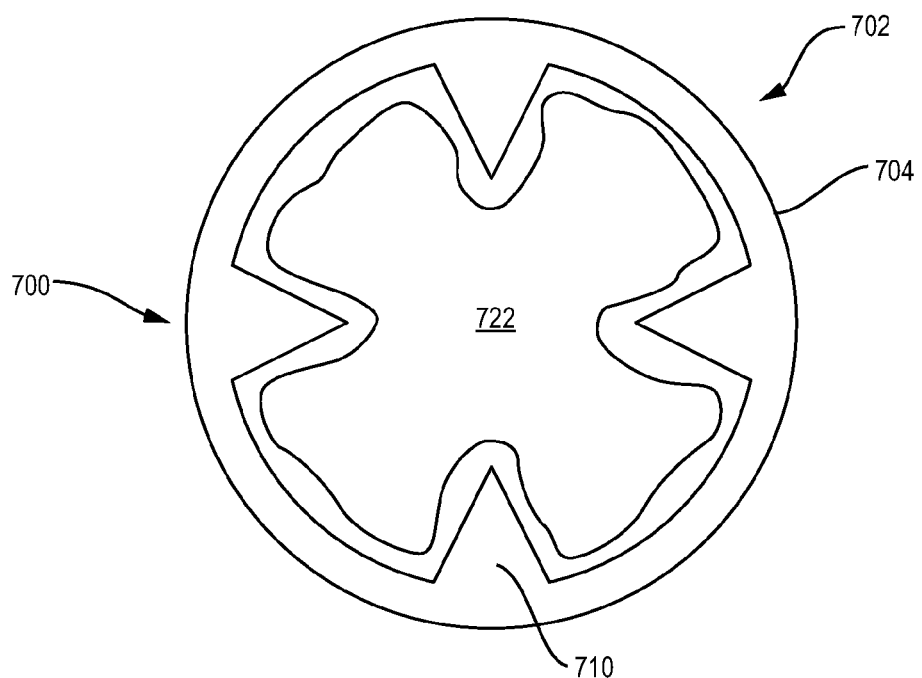
FIG. 9 is a top view of an exemplary reactor system having a heat exchange module incorporated into an outer support structure.

FIG. 9 is a top view of the exemplary reactor system 700 shown in FIGS. 7 and 8 together with an inner reactor container 722. The system includes a heat exchange module 702 that is integrally formed as part of the outer support structure 704 wherein the heat exchange module 702 contacts the inner container 722. The baffled portion 710 of the heat exchanger module 702 contacts the inner container 722 in a manner so as to provide a baffle structure on the interior of the inner container 722 yielding increased mixing.

Figure 10:
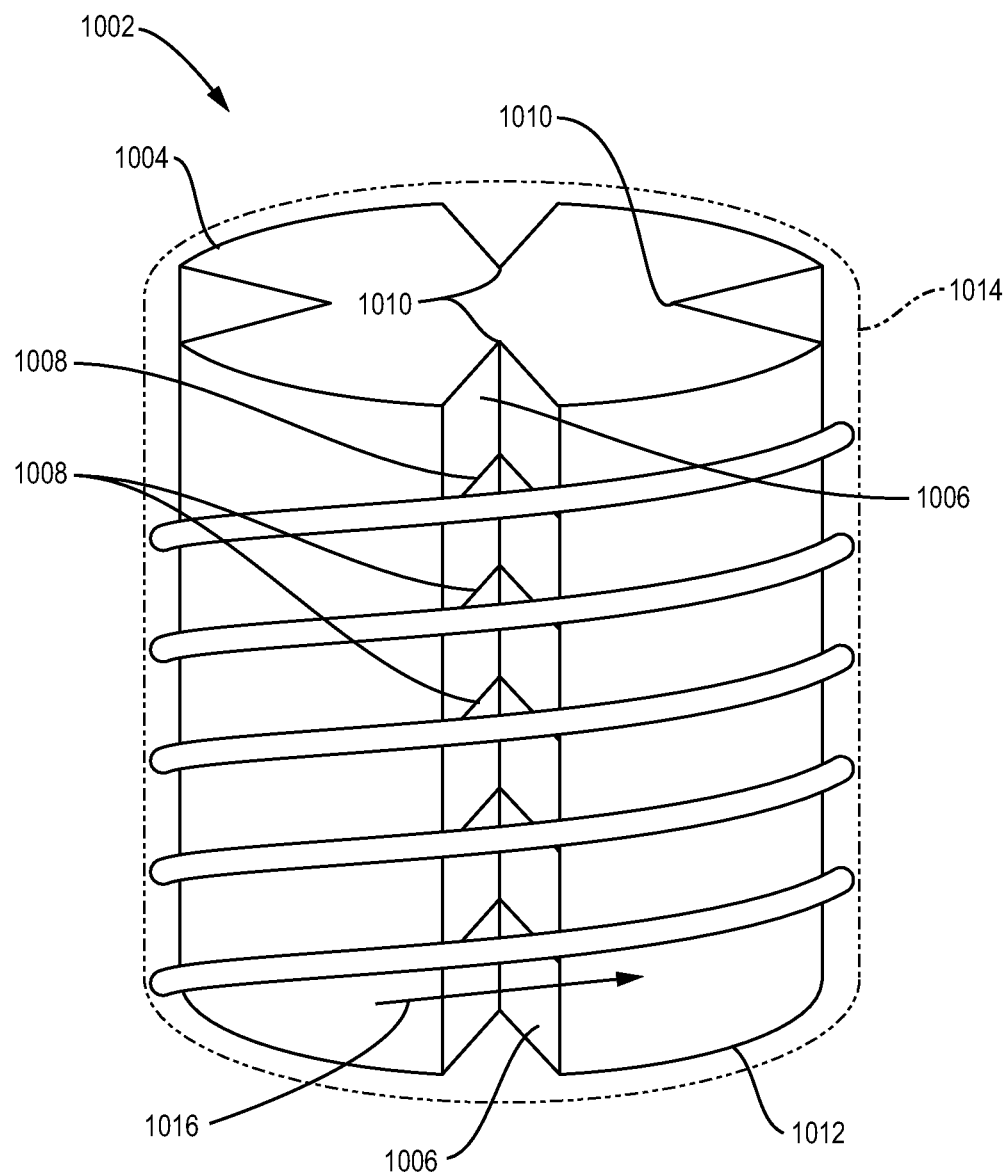
FIG. 10 is a perspective view of an exemplary heat exchange module having a serpentine flow path.
Figure 11:
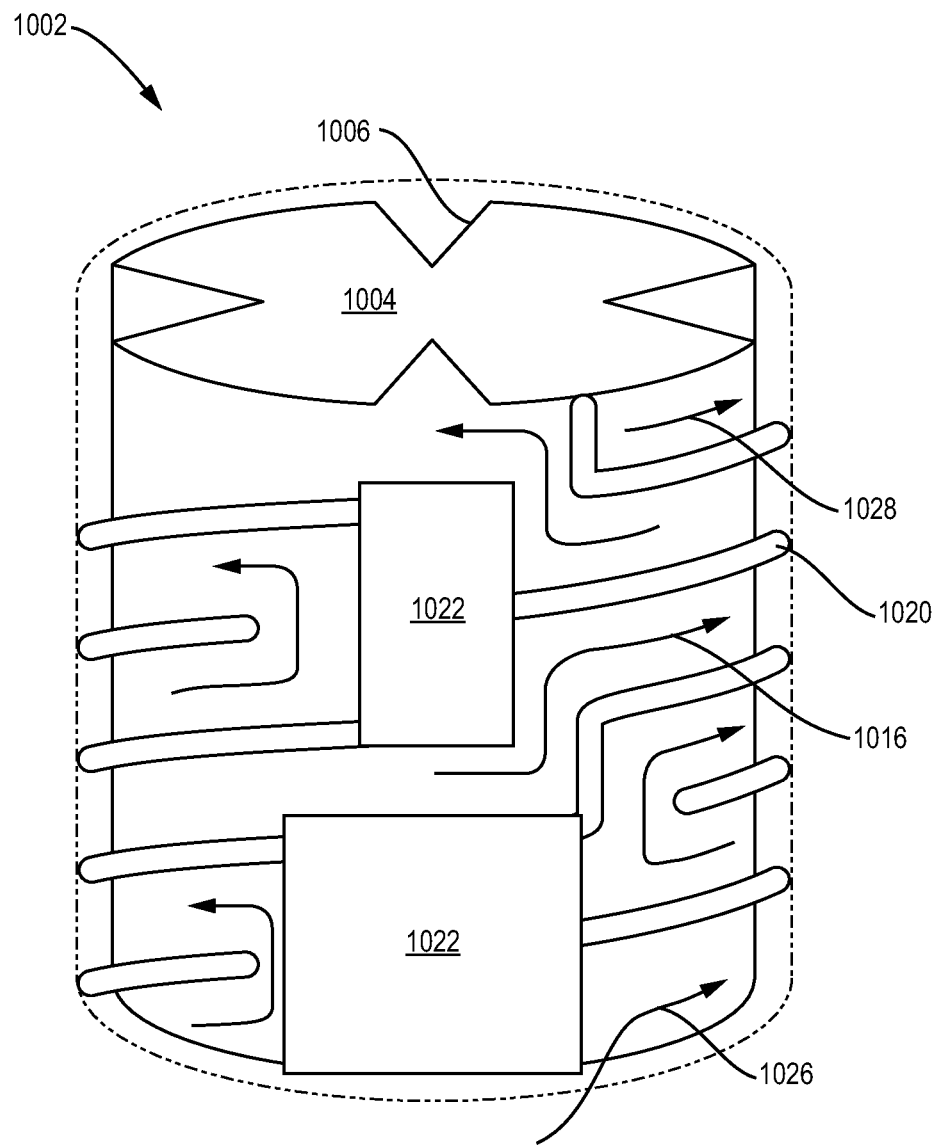
FIG. 11 is a perspective view of an exemplary heat exchange module having a non-linear flow path and an opening configured for alignment with a window.

FIGS. 10-11 depict embodiments wherein the heat exchanger module 1002 is integrally formed with the outer support structure (shown in phantom) and a temperature control fluid flow path is created between the outer support structure and the heat exchanger module body 1004 surface. In FIG. 10, an exemplary heat exchange module 1002 having an integral baffle 1006 with a non-linear fluid flow path created by various separator plates 1008 disposed vertically along the baffle channels 1006 is shown. In this embodiment the body 1004 of the heat exchange module 1002 is again integrally formed on an outer support structure (not shown). The body 1004 contains protrusions 1010 into the interior of the vessel, which form baffle channels 1006. Temperature control fluid can circulate along a path between the outer support structure (not shown) and the surface of the body 1004, including through the baffle channels 1006. Separator plates 1008 can be formed along the length of the baffle channel 1006 so as to direct the flow of fluid in a desired path. In the baffle channel 1006, the separator plates 1008 will stop fluid from flowing vertically from the bottom 1012 of the heat exchange module 1002 to the top 1014 of the heat exchange module 1002 or from the top to the bottom. One skilled in the art will recognize the advantages of directing the fluid flow pattern around the heat exchange module 1002 to achieve the desired heat transfer characteristics for the system.

In some embodiments, the fluid flow path 1016 within the heat exchange module 1002 can be directed in a non-linear direction concentrically around the heat exchanger module 1002. FIG. 10 depicts a spiral channel structure 1018 to direct the temperature control fluid around the heat exchange module 1002 that is integrally formed with the outer support surface (not shown). Separator plates 1008 can be used to block vertical fluid flow through the baffle channels 1006 to prevent fluid from flowing vertically through the baffle 1006, which could short cut the remainder of the jacket. The spiral channel structure 1018 can be formed integrally with the body 1004, or can be formed removably and separately from the body 1004. The spiral channel structure 1018 can comprise a strip, tube, pipe, or other protrusion formed of metal, plastic, or any other non-porous, non-corrosive material, disposed in a concentric loop through the heat exchange module 1002 to direct fluid along a path 1016. The fluid circulation path 1016 should be sure to reach the protruded baffle channels 1006 to ensure the desired amount of temperature control therein. In other embodiments a tiered channel structure can be used to create a non-linear fluid circulation path.

FIG. 11 is a perspective view of an exemplary heat exchange module 1002 having at least one baffle 1006 and a tiered channel structure 1020 with a non-linear flow path 1016 and at least one opening 1022 configured for alignment with a window in the outer support structure (shown in phantom). A tiered, or terraced, interior channel structure 1020 is shown in FIG. 11 to direct temperature control fluid around the heat exchanger module 1002 and into the protrusions 1010 extending to the interior of the vessel 1024. In this embodiment the fluid follows the non-linear path 1016. The channel structure 1020 can have a fluid inlet 1026 at the bottom of the heat exchange module 1002 and an outlet 1028 at the top of the heat exchange module 1002, or alternatively, the heat exchange module 1002 can have temperature control inlet 1026 and outlet 1028 ports at any position so as to achieve the desired heat transfer results. As is shown, the heat exchange module 1002 can be formed to accommodate sight windows 1022 into the interior of the reactor system 1024 allowing an operator to monitor the reaction. The terraced baffle structure can allow the temperature control fluid circulation path to be directed around said sight windows 1022 to avoid the obstruction of the sight path. This non-linear circulation path 1016 can also allow any access ports or probes to be accessible to the outside of the support structure (not shown) as necessary.

Figure 12:
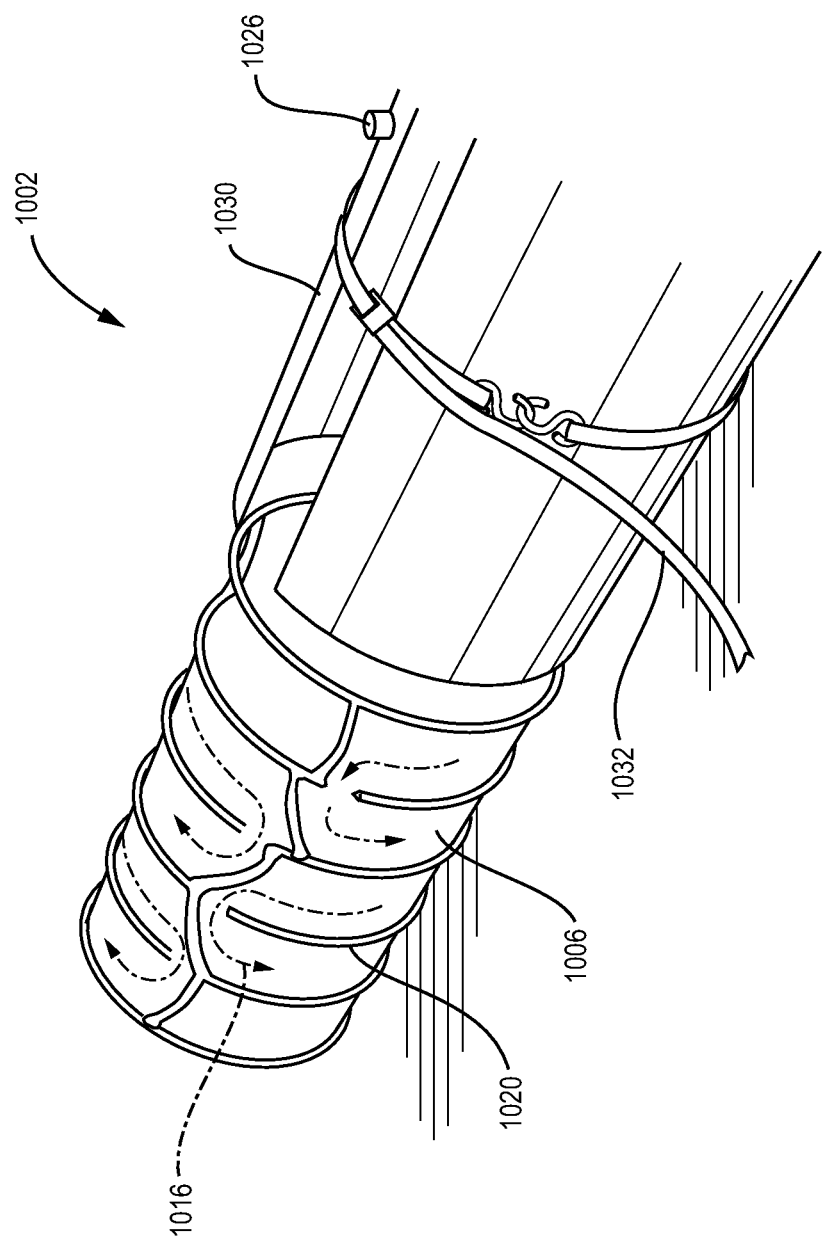
FIG. 12 is a perspective view of an exemplary embodiment of a reactor system having a jacketed, tiered baffle, bioreactor tank for routing a liquid coolant around the outer tank surface.

FIG. 12 is a perspective view of an exemplary embodiment of a heat exchanger module 1002. A jacketed, tiered baffle, bioreactor tank 1002 includes an outer cylindrical-shaped jacket 1030; and a cylindrical tank 1020 having an inner tank surface defining a chamber configured for supporting a flexible bag disposed within the chamber, and an outer tank surface having tiered baffles 1006 configured for routing a liquid coolant as shown by directional arrows 1016 around the entirety of the outer tank surface, the cylindrical tank disposed axially within the outer cylindrical-shaped jacket 1030, wherein the outer cylindrical-shaped jacket 1030 is sealed to the cylindrical tank in a manner sufficient to prevent or minimize loss of the liquid coolant that enters the system through port 1026. In constructing the system, strapping 1032 is used to help attach the jacket 1030 to the tank 1020 following its insertion in the jacket.

The heat exchanger formed from the inner, tiered, fluid channel 1020 and the outer support structure 1030 with the temperature control fluid flowing therebetween. The heat exchange module 1002 includes a body 1020 comprising an inner, tiered, fluid channel. The inlet tube 1026 can be configured to allow temperature control fluid to enter the module 1002 formed by the barrel 1020 and the outer jacket 1030. Alternatively, the outer jacket 1030 can be conically formed, utilizing seals known in the art to seal the module 1002.

Liner Embodiment

As shown in FIG. 13, some embodiments of the heat exchange module 1300 can comprise a removable, non-integral liner 1304 that can be disposed between an inner container 1302 and an outer support structure 1306. In some embodiments, the liner 1304 can be formed of a flexible material. Alternatively, the liner can be a non-collapsible liner. For instance, the liner 1304 can be made of a semi-rigid material cylindrically formed. The liner 1304 can be maintained between an inner reactor vessel or container 1302 and the outer support structure 1306 by any suitable method such as by friction, pressure (for example, pressure exerted on the surfaces upon expansion of the collapsible bag), gravity, fastening with screws, pegs, clamps, or the like, and use of adhesives. The liner 1304 can include a temperature control fluid inlet 1308 and outlet 1310, which can be fed through ports 1314 and 1316.

The liner can have channel segments 1312 creating a non-linear flow path between the inlet 1308 and the outlet 1310. Compared to a liner without welds or channels, the presence of a channel within the liner can result in a longer path for bulk fluid flow permitting fluid to be cooled or heated uniformly for a longer period of time. A channel can also prevent or reduce "dead zones" that can lead, for example, to non-uniform heating or cooling of fluid.

A channel defines a bulk fluid flow pathway through the liner; that is, a fluid flowing from a first portion to a second portion of the liner can flow in a predetermined orientation and/or at a predetermined flow rate by applying a pressure differential between the first and second portions. This and other configurations comprising channels can reduce the amount of random or non-directed fluid flow, for example, turbulence, eddies, and so forth, in the collapsible liner. A temperature control fluid can then be pumped through the channels created in the flexible liner.

Figure 14A:
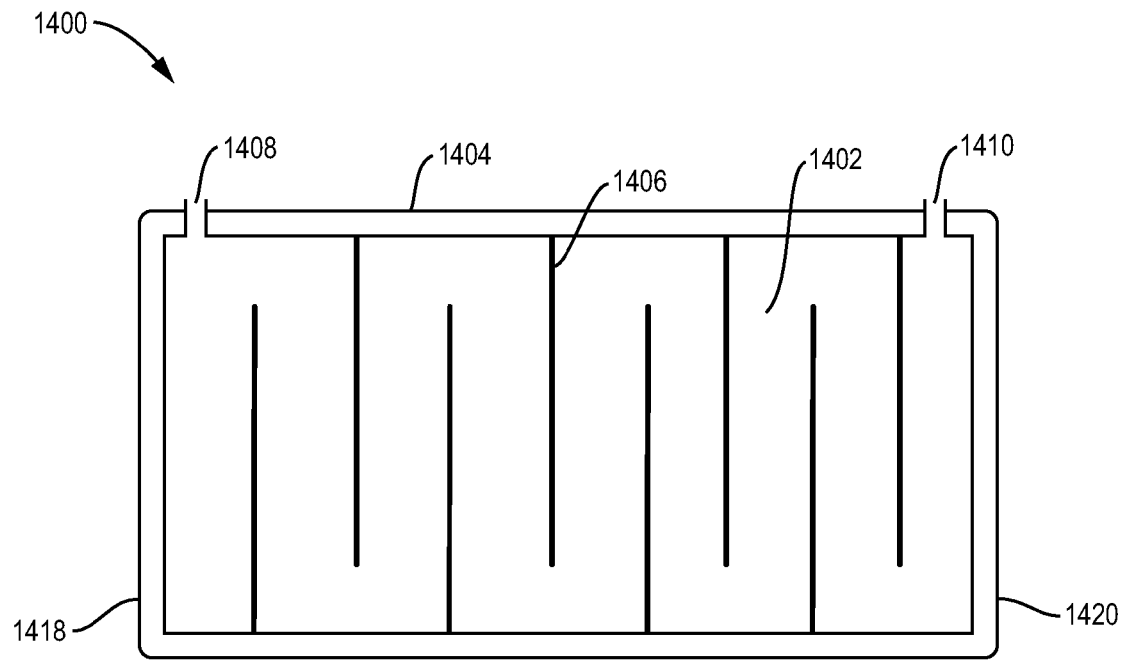
FIG. 14A is a cross-sectional view of a heat exchange module comprising a liner having vertical channel segments according to the invention.

As shown in FIGS. 14A-16B, the channel segment 1402 can form any non-linear fluid-flow path. FIG. 14A is a cross-sectional view of a heat exchange module 1400 comprising a liner 1404 having vertical channel segments 1402. Welds 1406 form the channel segments 1402 in the liner 1404 thus producing the desired fluid flow path, connecting an inlet 1408 and an outlet 1410. The inlet 1408 and outlet 1410 can be disposed in any manner so as to allow fluid flow between the inlet 1408 and outlet 1410. For example the inlet 1408 and outlet 1410 can be placed on the top, bottom, or sides of the liner and the inlet 1408 and outlet 1410 can both be disposed on the same or differing sides. One skilled in the art will understand that placement of the inlet 1408 and outlet 1410 can be positioned in any operable position and can be chosen for the ease of use of an operator.

Figure 14B:
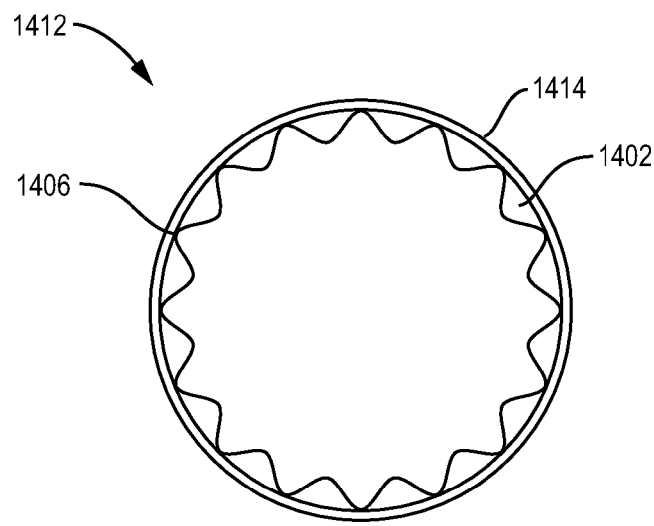
FIG. 14B is a top view of the liner of FIG. 14A as disposed in an exemplary reactor system.

The liner of FIG. 14A can be configured to form a cylindrical module 1412 configured to be disposed between the outer support structure 1414 and the interior of the vessel 1416, wherein an inner container (not shown) may be disposed. FIG. 14B is a top view of the liner 1404 of FIG. 14A as disposed in said cylindrical fashion. The left 1418 and right ends 1420 of the segmented liner 1404 in FIG. 14A can be joined and fused to form a cylindrical module 1412. In so doing the channel segments 1402 can be configured to face an interior of the vessel 1416 forming vertical segments, or corrugations.

Figure 15A:
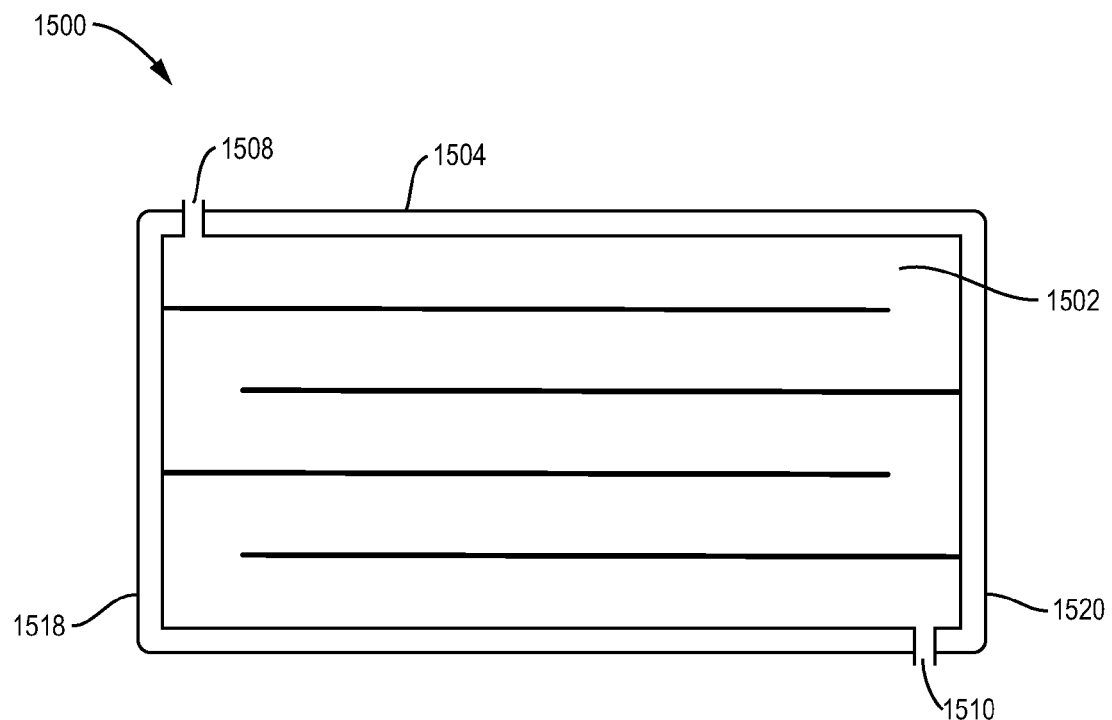
FIG. 15A is a cross-sectional view of a heat exchange module comprising a liner having horizontal channel segments according to the invention.
Figure 15B:
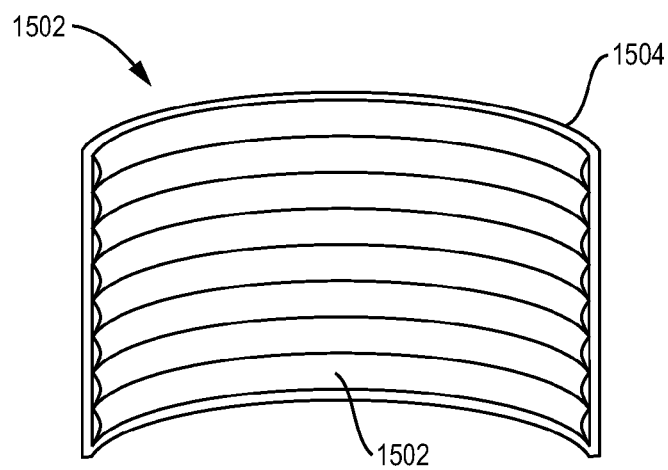
FIG. 15B is a cross-sectional view of the liner of FIG. 15A as disposed in an exemplary reactor system.

FIG. 15A is a cross-sectional view of a heat exchange module 1500 comprising a liner 1504 having horizontal channel segments 1502. The liner 1504 creates a fluid flow path between an inlet 1508 and an outlet 1510, wherein the segments 1502 define a non-linear flow path. The left 1518 and right ends 1520 of the segmented liner 1504 in FIG. 15A can be joined and fused to form a cylindrical module 1512. In so doing the channel segments 1502 can be configured to face an interior of the vessel forming horizontal segments or corrugations 1502. FIG. 15B is a cross-sectional view of the cylindrically formed liner of FIG. 15A having horizontal segments 1502.

Figure 16A:
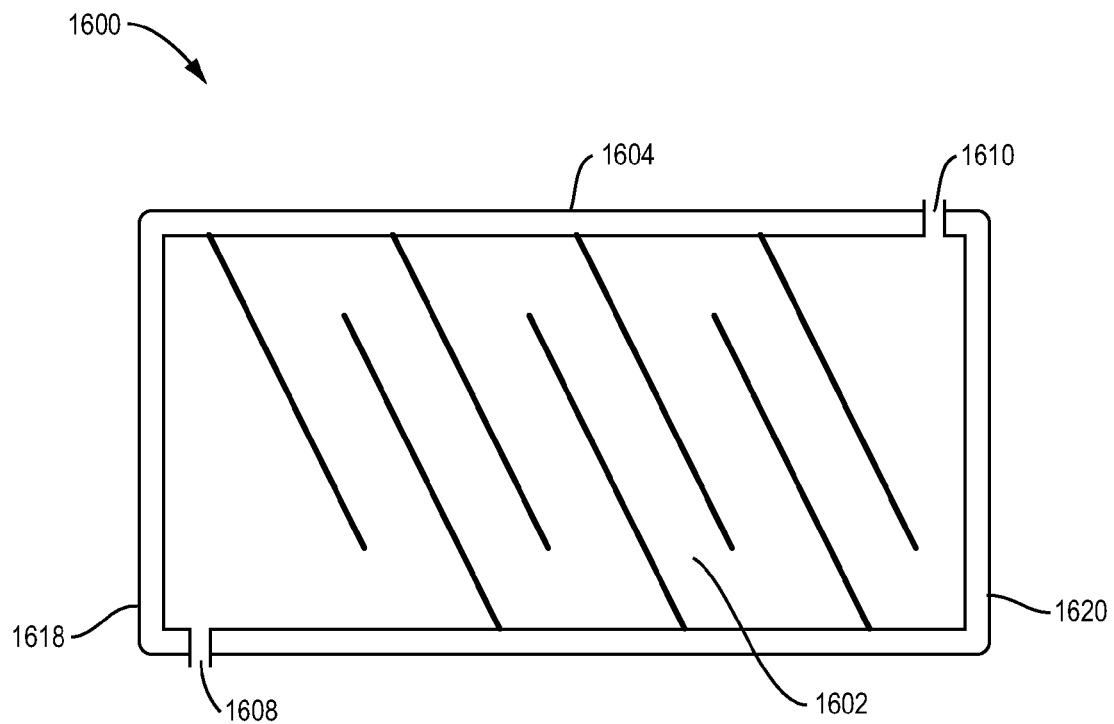
FIG. 16A is a cross-sectional view of a heat exchange module comprising a liner having helical channel segments according to the invention.
Figure 16B:
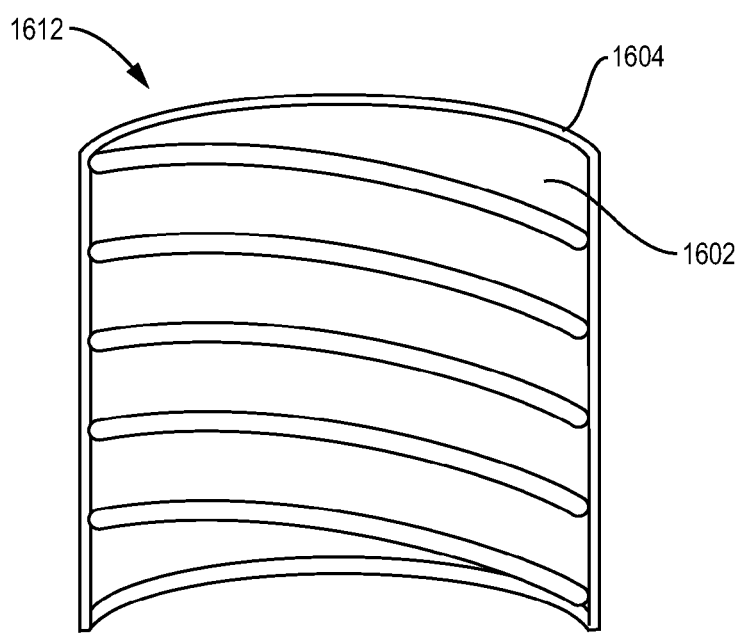
FIG. 16B is a cross-sectional view of the liner of FIG. 16A as disposed in an exemplary reactor system.

FIG. 16A is a cross-sectional view of a heat exchange module 1600 comprising a liner 1604 having helical channel segments 1602. The liner 1604 creates a fluid flow path between an inlet 1608 and an outlet 1610, wherein the segments 1602 define a non-linear flow path. The left 1618 and right ends 1620 of the segmented liner 1604 in FIG. 16A can be joined and fused to form a cylindrical module 1612. In so doing the channel segments 1602 can be configured to face an interior of the vessel 1616 forming helical segments or corrugations 1602. FIG. 16B is a cross-sectional view of the cylindrically formed liner 1612 of FIG. 16A as disposed in an exemplary reactor system.

Figure 17:
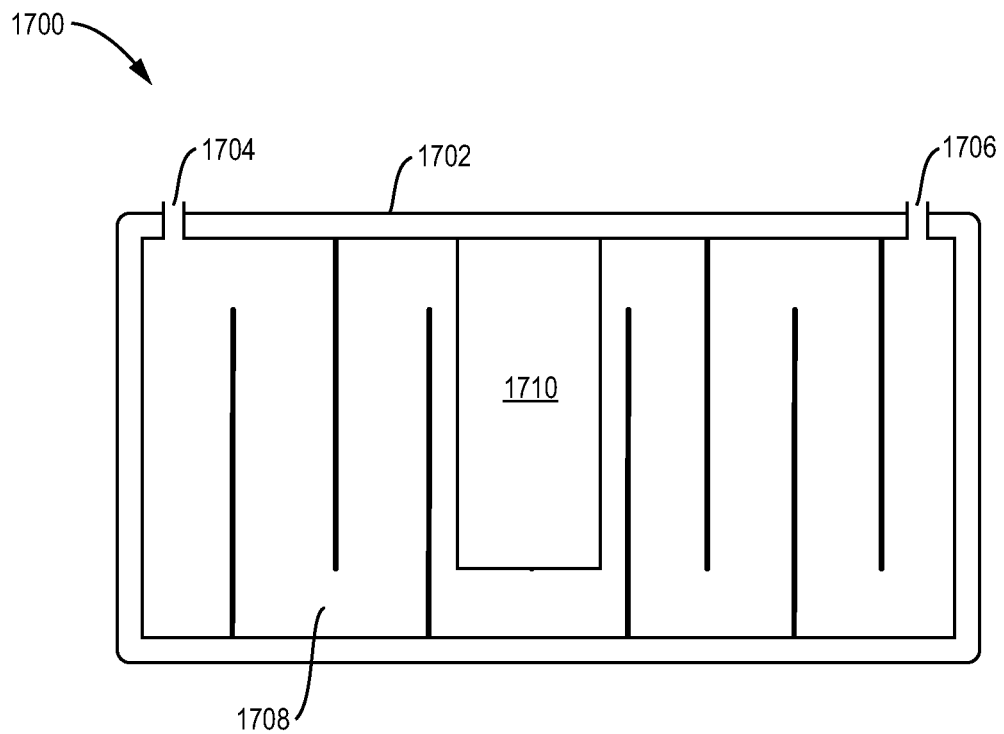
FIG. 17 is a cross-sectional view of a heat exchange module comprising a liner configured for alignment with a window.

FIG. 17 is a cross-sectional view of a heat exchange module 1700 comprising a liner 1702 configured for alignment with a window (not shown). The liner 1702 can contain an inlet 1704, an outlet 1706, a segmented flow path 1708 connecting the inlet 1704 and outlet 1706, and a window portion 1710 where there is no obstruction of vision through the liner 1702. In some embodiments, it may be desirable to configure the liner 1702 such that a user can have a sight path through the outer support structure (not shown), liner 1702, and into the inner container (not shown). For example, this can be achieved by having no liner material in the window portion 1710, with the edges of the window portion sealed and fused such that no fluid will leak into or out of the liner.

Figure 18:
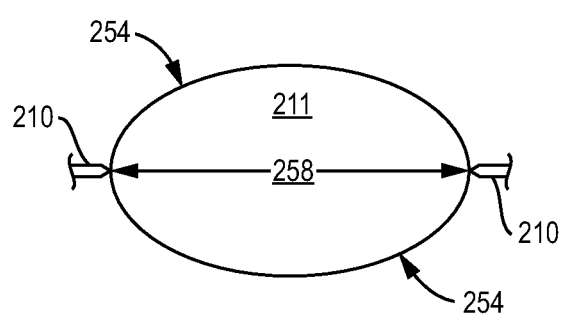
FIG. 18 is a cross-sectional view of an exemplary liner segment according to the present invention.

FIG. 18 is a cross-sectional view of an exemplary liner channel segment according to the present invention. It should be understood that welds 210 can be formed by any suitable process and, in some cases, can depend on the particular materials, such as thermally conductive material, used to form the container. Accordingly, a weld 210 can include any suitable joining of two or more wall portions, for example, two or more interior surface portions of a container, and can be achieved by methods such as welding, including, for example, heat welding and ultrasonic welding, use of the adhesive, clamping, fastening, or other attaching techniques.

The cross-sectional dimension of the channel formed in the liner can be designed to allow a particular flow rate, internal pressure, and/or length of time of fluid flow inside the bag. These parameters, in turn, can be chosen depending on, for example, the particular fluid to be flowed in the bag, the volume of the collapsible bag, the desired temperature change, and the like. Accordingly, depending on these and other factors, a channel 211 of the collapsible bag, at full expansion, or full collapse, of the collapsible bag, can have, for example, a maximum cross-sectional dimension 258 taken perpendicular to the centerline of the channel 211 of from about 1 centimeter to about 20 centimeters. In some embodiments, the maximum cross-sectional dimension 258 of a channel 211 portion is from about 5 centimeters to about 10 centimeters. The flexible liner channel segment can include a thermally conductive surface. A thermally conductive surface 254 can comprise a thermally conductive material as described herein.

Figure 19A:
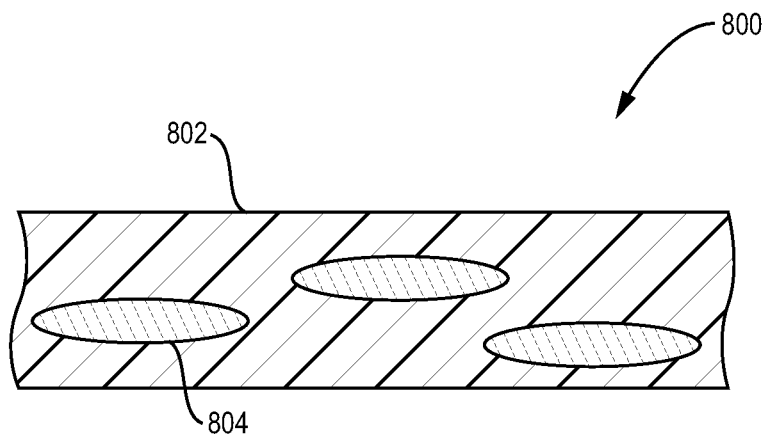
FIG. 19A is a sectional view of an inner or outer tubing film having sections of heat conductive material attached to the film.
Figure 19B:
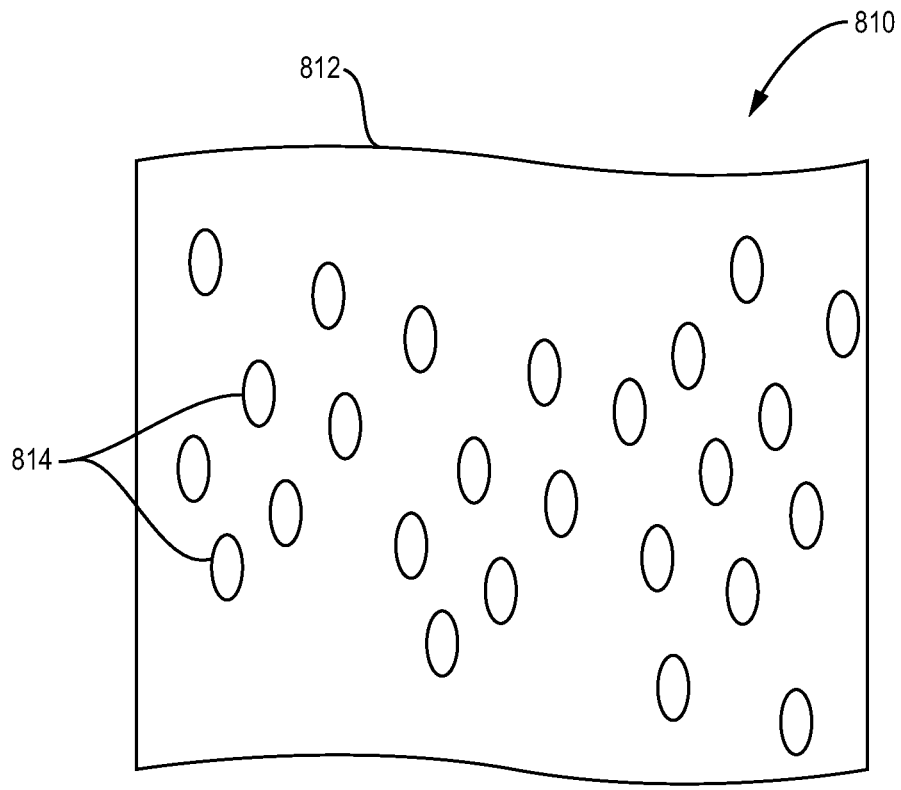
FIG. 19B is sectional view of an inner or outer bag film having sections of heat conductive material attached to the film.

FIGS. 19A and 19B, as described in more detail above, illustrate that a temperature-controlling surface can comprise a thermally conductive surface formed of a thermally conductive material, such as, e.g., a plurality of particles 804, 814, FIGS. 19A, 19B, respectively.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will readily appreciate that all parameters, dimensions, materials, and configurations described herein are meant to be exemplary and that the actual parameters, dimensions, materials, or configurations will depend upon the specific application for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention can be practiced otherwise than as specifically described and claimed. The present invention is directed to each individual feature, system, article, material, kit, and/or method described herein, and to any combination of the foregoing.

The indefinite articles "a" and "an," as used herein in the specification and in the claims, unless clearly indicated to the contrary, should be understood to mean "at least one." Throughout the description and claims of this specification, the words "comprise," "contain," "include," "having," "composed of," and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

It should also be understood that, unless clearly indicated to the contrary, in any methods claimed herein that include more than one step or act, the order of the steps or acts of the method is not necessarily limited to the order in which the steps or acts of the method are recited.

Features groups described in conjunction with a particular aspect of the invention are to be understood to be applicable to any other aspect described herein unless incompatible therewith. All of the features disclosed in the specification, and claims, abstract and drawings, and/or all of the steps of any method or process disclosed, can be combined in any combination, except combinations where at least some of such features or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. All publications and references cited herein are expressly incorporated herein by reference in their entirety.

What is claimed is:

1. A heat exchange module for use in a chemical, pharmaceutical or biological reactor system, comprising:
    a body configured to be disposed in a reactor vessel comprising a support structure, the reactor vessel having an inner replaceable or single use reactant container, the body comprising at least one surface configured to conform to a shape of the reactor vessel and at least one thermally conductive surface adapted to contact the inner replaceable container to facilitate heat transfer, and a heat exchanger disposed within the body comprising a fluid circulation path through which a heat exchange fluid is circulated; wherein said heat exchanger fluid circulation path comprises:

an elongate tube axially positioned within the body and extending substantially the length of the body, the elongate tube configured for delivering the heat exchange fluid through the elongate tube to an opening at the bottom of the elongate tube; and a flow path of the heat exchange fluid from the opening at the bottom of the elongate tube to an outlet or an outlet tube at the top end of the body.

2. The heat exchange module of claim 1 wherein the body further comprises a coupler for attaching the module to the reactor vessel.

3. The heat exchange module of claim 2 wherein the coupler is a bracket or hook for attaching the module to a top portion of the reactor vessel.

4. The heat exchange module of claim 1 wherein the body is configured to extend to a position opposite an impeller positioned at or near the bottom of the inner replaceable container, the body configured as a baffle to baffle a shear field produced by the impeller.

5. A heat exchange module for use in a chemical, pharmaceutical or biological reactor system, comprising:

a body configured to be disposed in a reactor vessel comprising a support structure and having an inner replaceable or single use reactant container, the body further comprising at least one thermally conductive surface adapted to contact the inner replaceable reactantcontainer to facilitate heat transfer, and a heat exchanger disposed within the body comprising a fluid circulation path through which a heat exchange fluid is circulated; wherein said heat exchanger fluid circulation path comprises:

an elongate tube axially positioned within the body and extending substantially the length of the body, the elongate tube configured for delivering the heat exchange fluid through the elongate tube to an opening at the bottom of the elongate tube; and a flow path of the heat exchange fluid from the opening at the bottom of the elongate tube to an outlet or an outlet tube at the top end of the body.

6. The heat exchange module of claim 5, wherein the heat exchange module is integrally formed as a part of the reactor vessel and further comprises at least one baffle that provides the thermally conductive surface adapted to contact the inner replaceable reactant container and facilitate heat transfer.

7. The heat exchange module of claim 5, wherein the heat exchange module is integrally formed as part of the reactor vessel and the fluid circulation path further comprises atleast one non-linear channel disposed within a wall of the reactor vessel.

8. The heat exchange module of claim 5 wherein the non-linear channel further comprises at least one of spiral, serpentine and maze-like pathways configured to maintain thethermally conductive surface at a desired temperature.

9. The heat exchange module of claim 8 wherein the module further comprises an opening configured for alignment with a window in the outer support structure to facilitate viewing of the inner replaceable reactant container.

10. The heat exchange module of claim 5 wherein the module further comprises a liner configured for disposition between at least a portion of the reactor vessel and at least aportion of the inner replaceable reactant container.

11. The heat exchange module of claim 10 wherein the liner further comprises a segmentedjacket comprising at least one inlet, at least one outlet and a wall structure defining a non-linear inner fluid flow channel between the inlet and outlet.

12. The heat exchange module of claim 11 wherein the liner further comprises a polymeric material with a corrugated wall structure of interconnected segments that define the non-linear inner fluid flow channel between the inlet and outlet.

13. The heat exchange module of claim 11 wherein the segments are oriented horizontally, vertically or helically.

14. The heat exchange module of claim 11 wherein the jacket is configured to substantially surround a sidewall of the inner replaceable reactant container.

15. The heat exchange module of claim 14 wherein the jacket further comprises at least one opening configured for alignment with a window in the outer support structure to facilitate viewing of the inner container.

16. The heat exchange module of claim 14 wherein the jacket further comprises a thermally conductive material.

17. The heat exchange module of claim 16 wherein the thermally-conductive material further comprises a layer of thermally conductive material or a plurality of thermally-conductiveparticles disposed on or embedded in a surface of the module.

18. The heat exchange module of claim 14 wherein the jacket further comprises a plurality of inner protrusions configured to engage the inner replaceable reactant container.

* * * * *